(12) United States Patent
Gupta

(10) Patent No.: US 9,119,783 B2
(45) Date of Patent: *Sep. 1, 2015

(54) METHOD OF TREATING PULMONARY DISORDERS WITH LIPOSOMAL AMIKACIN FORMULATIONS

(75) Inventor: Renu Gupta, Moorestown, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,246

(22) Filed: May 24, 2012

(65) Prior Publication Data

US 2013/0089598 A1    Apr. 11, 2013

Related U.S. Application Data

(63) Continuation-in-part of application No. 12/250,412, filed on Oct. 13, 2008, which is a continuation-in-part of application No. PCT/US2008/062868, filed on May 7, 2008.

(60) Provisional application No. 61/489,940, filed on May 25, 2011, provisional application No. 60/916,342, filed on May 7, 2007.

(51) Int. Cl.
| | |
|---|---|
| A61K 9/127 | (2006.01) |
| A61K 31/7036 | (2006.01) |
| A61K 9/00 | (2006.01) |
| A61K 31/375 | (2006.01) |
| A61K 31/70 | (2006.01) |

(52) U.S. Cl.
CPC .............. *A61K 9/127* (2013.01); *A61K 9/0078* (2013.01); *A61K 31/375* (2013.01); *A61K 31/70* (2013.01); *A61K 31/7036* (2013.01)

(58) Field of Classification Search
CPC ...................................................... A61K 9/127
USPC ......................................................... 424/450
See application file for complete search history.

(56) References Cited

U.S. PATENT DOCUMENTS

| | | | |
|---|---|---|---|
| 4,235,871 A | 11/1980 | Papahadjopoulos et al. |
| 4,372,949 A | 2/1983 | Kodama et al. |
| 4,394,448 A | 7/1983 | Szoka, Jr. et al. |

(Continued)

FOREIGN PATENT DOCUMENTS

| | | |
|---|---|---|
| EP | 0069307 | 1/1983 |
| EP | 0274431 | 5/1994 |

(Continued)

OTHER PUBLICATIONS

Office Action for U.S. Appl. No. 12/598,830, mailed Mar. 7, 2012.

(Continued)

*Primary Examiner* — Gollamudi Kishore
(74) *Attorney, Agent, or Firm* — Cooley LLP

(57) ABSTRACT

Disclosed herein are methods of treating pulmonary disorders comprising administering to the patient an effective dose of a nebulized liposomal amikacin formulation for at least one treatment cycle, wherein: the treatment cycle comprises an administration period of 15 to 75 days, followed by an off period of 15 to 75 days; and the effective dose comprises 100 to 2500 mg of amikacin daily during the administration period.

35 Claims, 15 Drawing Sheets

(56) References Cited

U.S. PATENT DOCUMENTS

| | | |
|---|---|---|
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,963,367 A | 10/1990 | Ecanow |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |
| 5,041,278 A | 8/1991 | Janoff et al. |
| 5,049,388 A | 9/1991 | Knight et al. |
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,409,704 A | 4/1995 | Bally et al. |
| 5,459,127 A | 10/1995 | Felgner et al. |
| 5,508,269 A | 4/1996 | Smith et al. |
| 5,540,936 A | 7/1996 | Coe et al. |
| 5,543,152 A | 8/1996 | Webb et al. |
| 5,569,464 A | 10/1996 | Endo et al. |
| 5,578,320 A | 11/1996 | Janoff et al. |
| 5,610,198 A | 3/1997 | Barry, III et al. |
| 5,616,334 A | 4/1997 | Janoff et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Lagace et al. |
| 5,665,383 A | 9/1997 | Grinstaff et al. |
| 5,723,147 A | 3/1998 | Kim et al. |
| 5,736,155 A | 4/1998 | Bally et al. |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,820,848 A | 10/1998 | Boni et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,922,350 A | 7/1999 | Janoff et al. |
| 5,945,122 A | 8/1999 | Abra et al. |
| 5,958,449 A | 9/1999 | Hersch et al. |
| 5,993,850 A | 11/1999 | Sankaram et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,086,851 A | 7/2000 | Boni et al. |
| 6,090,407 A | 7/2000 | Knight et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,211,162 B1 | 4/2001 | Dale et al. |
| 6,221,388 B1 | 4/2001 | Hersch et al. |
| 6,274,175 B1 | 8/2001 | Gombotz et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,521,211 B1 | 2/2003 | Unger et al. |
| 6,521,736 B2 | 2/2003 | Watterson et al. |
| 6,596,305 B1 | 7/2003 | Edgerly-Plug |
| 6,599,912 B1 | 7/2003 | Au et al. |
| 6,613,352 B2 | 9/2003 | Lagace et al. |
| 6,615,824 B2 | 9/2003 | Power |
| 6,843,942 B2 | 1/2005 | Katinger et al. |
| 6,855,296 B1 | 2/2005 | Baker et al. |
| 6,900,184 B2 | 5/2005 | Cohen et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,991,809 B2 | 1/2006 | Anderson |
| 7,063,860 B2 | 6/2006 | Chancellor et al. |
| 7,100,600 B2 | 9/2006 | Loeffler et al. |
| 7,331,339 B2 | 2/2008 | Smith et al. |
| 7,368,102 B2 | 5/2008 | Tarara et al. |
| 7,544,369 B2 | 6/2009 | Boni et al. |
| 7,600,511 B2 | 10/2009 | Power et al. |
| 7,718,189 B2 | 5/2010 | Boni et al. |
| 7,748,377 B2 | 7/2010 | Smith et al. |
| 7,879,351 B2 | 2/2011 | Li et al. |
| 7,971,588 B2 | 7/2011 | Fink et al. |
| 8,100,162 B2 | 1/2012 | Joern et al. |
| 8,226,975 B2 | 7/2012 | Weers |
| 8,632,804 B2 | 1/2014 | Weers |
| 8,642,075 B2 | 2/2014 | Weers |
| 8,673,348 B2 | 3/2014 | Weers |
| 8,673,349 B2 | 3/2014 | Weers |
| 8,679,532 B2 | 3/2014 | Weers |
| 8,802,137 B2 | 8/2014 | Boni et al. |
| 2001/0006660 A1 | 7/2001 | Lagace et al. |
| 2002/0035061 A1 | 3/2002 | Krieger et al. |
| 2002/0052390 A1 | 3/2002 | Krieger et al. |
| 2002/0086852 A1 | 7/2002 | Cantor et al. |
| 2002/0187105 A1 | 12/2002 | Zou et al. |
| 2003/0059375 A1 | 3/2003 | Perez-Soler et al. |
| 2003/0118636 A1 | 6/2003 | Friesen et al. |
| 2003/0138481 A1 | 7/2003 | Zadi |
| 2003/0224039 A1 | 12/2003 | Boni et al. |
| 2004/0009126 A1 | 1/2004 | Pilkiewicz et al. |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2005/0019926 A1 | 1/2005 | Gonda et al. |

(56) References Cited

U.S. PATENT DOCUMENTS

| | | |
|---|---|---|
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0220752 A1 | 10/2005 | Charmot et al. |
| 2005/0249795 A1 | 11/2005 | Zhang et al. |
| 2006/0067998 A1 | 3/2006 | Kurzrock et al. |
| 2006/0073198 A1 | 4/2006 | Boni et al. |
| 2006/0217603 A1 | 9/2006 | Nagai et al. |
| 2007/0077290 A1 | 4/2007 | Li et al. |
| 2007/0081963 A1 | 4/2007 | Oh et al. |
| 2007/0196461 A1 | 8/2007 | Weers |
| 2007/0267010 A1 | 11/2007 | Fink et al. |
| 2008/0089927 A1 | 4/2008 | Malinin |
| 2008/0246472 A1 | 10/2008 | Igney et al. |
| 2009/0104256 A1 | 4/2009 | Gupta |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0159079 A1 | 6/2011 | Li et al. |
| 2012/0010162 A1 | 1/2012 | Norling |
| 2012/0244206 A1 | 9/2012 | Cipolla et al. |
| 2013/0028960 A1 | 1/2013 | Weers |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0136788 A1 | 5/2013 | Gupta |
| 2013/0330400 A1 | 12/2013 | Perkins et al. |
| 2014/0072620 A1 | 3/2014 | Weers |
| 2014/0314835 A1 | 10/2014 | Boni et al. |

FOREIGN PATENT DOCUMENTS

| | | |
|---|---|---|
| EP | 2457609 | 5/2012 |
| GB | 2145107 | 3/1985 |
| JP | 63-500175 | 1/1988 |
| JP | 63-239213 | 5/1988 |
| JP | 10-511363 | 11/1998 |
| JP | 2006-028069 | 2/2006 |
| UA | 27298 | 10/2007 |
| UA | 27804 | 11/2007 |
| WO | WO 85/00968 | 3/1985 |
| WO | WO 86/06959 | 12/1986 |
| WO | WO 87/00043 | 1/1987 |
| WO | WO 87/02219 | 4/1987 |
| WO | WO 88/04573 | 6/1988 |
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 97/29851 | 8/1997 |
| WO | WO 99/30686 | 6/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/05373 | 1/2001 |
| WO | WO 01/18280 | 3/2001 |
| WO | WO 01/32246 | 5/2001 |
| WO | WO 02/32400 | 4/2002 |
| WO | WO 02/43699 | 6/2002 |
| WO | WO 03/045965 | 6/2003 |
| WO | WO 03/75889 | 9/2003 |
| WO | WO 03/075890 | 9/2003 |
| WO | WO 2004/002453 | 1/2004 |
| WO | WO 2004/047802 | 6/2004 |
| WO | WO 2004/054499 | 7/2004 |
| WO | WO 2004/110346 | 12/2004 |
| WO | WO 2006/108556 | 10/2006 |
| WO | WO 2007/011940 | 1/2007 |
| WO | WO 2007/067520 | 6/2007 |
| WO | WO 2007/117509 | 10/2007 |
| WO | WO 2007/117550 | 10/2007 |
| WO | WO 2008/137717 | 11/2008 |
| WO | WO 2008/137917 | 11/2008 |
| WO | WO 2010/045209 | 4/2010 |
| WO | WO 2013/177226 | 11/2013 |
| WO | WO 2015/017807 | 2/2015 |

OTHER PUBLICATIONS

International Search Report and Written Opinion for International Application No. PCT/US2008/062469, mailed Sep. 18, 2008.
International Preliminary Report on Patentability for International Application No. PCT/US2008/062469, dated Nov. 10, 2009.
Office Action for U.S. Appl. No. 12/250,412, mailed Dec. 2, 2011.
Office Action for U.S. Appl. No. 12/250,412, mailed Jun. 27, 2011.
International Search Report and Written Opinion for International Application No. PCT/US2008/062868, mailed Sep. 18, 2008.
International Preliminary Report on Patentability for International Application No. PCT/US2008/062868, dated Nov. 10, 2009.
Examination Report for Australian Patent Application No. 2009303542, dated Jun. 20, 2012.
Office Action for Chinese Patent Application No. 200980140740.2, dated Jul. 3, 2012.
Office Action for New Zealand Patent Application No. 592217, mailed Sep. 1, 2011.
Written Opinion for International Application No. PCT/US2009/060468, mailed Jun. 24, 2010.
International Preliminary Report on Patentability for International Application No. PCT/US2009/060468, dated Apr. 19, 2011.
Office Action for Australian Patent Application No. 2003304204, mailed Jun. 25, 2008.
Office Action for Canadian Patent Application No. 2504317, dated Jan. 27, 2011.
Office Action for Canadian Patent Application No. 2504317, dated Jun. 16, 2010.
First Office Action for Chinese Patent Application No. 200380106534.2, dated Aug. 11, 2006.
Second Office Action for Chinese Patent Application No. 200380106534.2 [no date].
Third Office Action for Chinese Patent Application No. 200380106534.2, dated May 22, 2009.
Supplementary European Search Report for European Application No. 03816990.0, mailed Jan. 12, 2009.
Summons to Attend Oral Hearing for European Application No. 03816990.0, mailed Dec. 21, 2011.
Office Action for European Application No. 03816990.0, mailed Jun. 17, 2011.
Office Action for European Application No. 03816990.0, mailed Apr. 24, 2009.
Office Action for European Application No. 03816990.0, mailed Jun. 5, 2012.
Office Action for Israel Patent Application No. 168279, dated Nov. 3, 2010.
Office Action for Israel Patent Application No. 168279, dated Aug. 17, 2009.
Office Action for Israel Patent Application No. 168279, dated Jun. 23, 2008.
Office Action for Indian Patent Application No. 2219/delnp/2005, dated Jan. 3, 2007.
Decision of Refusal for Japanese Patent Application No. 2005-500829, dated Feb. 14, 2012.
Notification of Reasons for Refusal for Japanese Patent Application No. 2005-500829, dated Feb. 15, 2011.
Notification of Reasons for Refusal for Japanese Patent Application No. 2005-500829, dated Jul. 6, 2010.
Office Action for Korean Patent Application No. 10-2005-7007679, dated Dec. 26, 2011.

(56) References Cited

OTHER PUBLICATIONS

Office Action for Korean Patent Application No. 10-2005-7007679, dated Jan. 18, 2011.
Office Action for Mexican Patent Application No. PA/a/2005/004580, mailed Aug. 25, 2009.
Third Office Action for Mexican Patent Application No. PA/a/2005/004580, mailed Dec. 10, 2008.
Second Office Action for Mexican Patent Application No. PA/a/2005/004580, mailed May 9, 2008.
First Office Action for Mexican Patent Application No. PA/a/2005/004580, mailed Jan. 30, 2008.
Office Action for New Zealand Patent Application No. 540087, dated Jan. 4, 2008.
Office Action for New Zealand Patent Application No. 540087, dated Sep. 14, 2006.
Office Action for U.S. Appl. No. 10/696,389, mailed Nov. 14, 2008.
Office Action for U.S. Appl. No. 10/696,389, mailed Mar. 28, 2008.
Office Action for U.S. Appl. No. 10/696,389, mailed Oct. 10, 2007.
Office Action for U.S. Appl. No. 10/696,389, mailed Apr. 2, 2007.
International Search Report for International Application No. PCT/US2003/034240, mailed Jul. 12, 2005.
Office Action for Mexican Patent Application No. MX/a/2010/000195, mailed Feb. 1, 2012.
Office Action for Mexican Patent Application No. MX/a/2010/000195, mailed Jul. 27, 2011.
Office Action for New Zealand Patent Application No. 564543, mailed Jan. 4, 2008.
Examiner's First Report for Australian Application No. 2006270008, dated Dec. 10, 2010.
Second Office Action for Chinese Patent Application No. 200680034397.X, dated Feb. 9, 2011.
First Office Action for Chinese Patent Application No. 200680034397.X, dated Jan. 22, 2010.
Office Action for Egyptian Patent Application No. PCT 84/2008.
Supplementary European Search Report for European Application No. 06787716.7, mailed Dec. 29, 2011.
Office Action for Israel Patent Application No. 188406, dated Jun. 13, 2011.
Office Action for Israel Patent Application No. 188406, dated Apr. 26, 2010.
Office Action for Japanese Patent Application No. 2008-522895, dated Apr. 17, 2012.
Office Action for Mexican Patent Application No. MX/a/2008/000425, dated Jun. 2, 2010.
Office Action for New Zealand Patent Application No. 565300, dated Feb. 24, 2011.
Office Action for New Zealand Patent Application No. 565300, dated Nov. 11, 2009.
Office Action for New Zealand Patent Application No. 565300, dated May 31, 2011.
Office Action for U.S. Appl. No. 11/185,448, mailed Dec. 17, 2009.
Office Action for U.S. Appl. No. 11/185,448, mailed Jun. 30, 2009.
International Search Report and Written Opinion for International Application No. PCT/US2006/027859, mailed Aug. 14, 2007.
International Preliminary Report on Patentability for International Application No. PCT/US2006/027859, dated Jan. 22, 2008.
Office Action for Mexican Patent Application No. MX/a/2008/012684, dated Jul. 8, 2011.
Office Action for Mexican Patent Application No. MX/a/2008/012684, dated Apr. 5, 2011.
Office Action for U.S. Appl. No. 11/398,859, mailed Jun. 4, 2010.
Office Action for U.S. Appl. No. 11/398,859, mailed Sep. 11, 2009.
International Search Report and Written Opinion for International Application No. PCT/US2007/008404, mailed Sep. 26, 2008.
International Preliminary Report on Patentability for International Application No. PCT/US2007/008404, dated Oct. 21, 2008.
European Search Report for European Patent Application No. 11159754, mailed Jun. 22, 2011.
Office Action for U.S. Appl. No. 12/424,177, mailed Mar. 16, 2012.
Office Action for U.S. Appl. No. 12/424,177, mailed Aug. 31, 2011.
Office Action for Australian Patent Application No. 2006322076, mailed Sep. 23, 2011.
Office Action for Japanese Patent Application No. 2008-544430, mailed May 26, 2012.
Office Action for U.S. Appl. No. 11/634,343, mailed Jan. 17, 2012.
Office Action for U.S. Appl. No. 11/634,343, mailed Aug. 4, 2011.
Office Action for U.S. Appl. No. 11/634,343, mailed Apr. 5, 2011.
Office Action for U.S. Appl. No. 11/634,343, mailed Sep. 14, 2010.
Office Action for U.S. Appl. No. 11/634,343, mailed Feb. 23, 2010.
Office Action for U.S. Appl. No. 11/634,343, mailed Jun. 19, 2009.
International Search Report and Written Opinion for International Application No. PCT/US2006/046360, mailed Oct. 17, 2007.
International Preliminary Report on Patentability for International Application No. PCT/US2006/046360, dated Jun. 11, 2008.
Office Action for U.S. Appl. No. 11/696,343, mailed Oct. 21, 2011.
Office Action for U.S. Appl. No. 11/696,343, mailed May 10, 2011.
International Search Report and Written Opinion for International Application No. PCT/US2007/008500, mailed Sep. 26, 2008.
International Preliminary Report on Patentability for International Application No. PCT/US2007/008500, dated Oct. 21, 2008.
Zhang, X. et al., "Antibacterial drug treatment of community acquired pneumonia," Chinese Journal of Respiratory and Critical Care Medicine, 4(4):258-260 (2005).
Huang, L. et al., "Progress of liposome's applications in biomedicine," International Journal of Biologicals, 29(3):130-132 and 137 (2006).
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against *Pseudomonas aeruginosa* in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in *Klebsiella pneumoniae*-infected lung tissue," The Journal Infectious Diseases, 171:938-947 (1995).
Ball, V. et al., "Complexation mechanism of bovine serum albumin and poly(allylamine hydrochloride)," J. Phys. Chem. B., 106(9):2357-2364 (2002).
Bangham, A. D., Introduction, "Liposomes: An Historical Perspective," in: Liposomes, Ostro, M. J. (ed.), pp. 1-29, Marcel Dekker, Inc., New York (1983).
Bargoni, A. et al., "Transmucosal transport of tobramycin incorporated in solid lipid nanoparticles (SLN) after duodenal administration to rats. Part I I—Tissue distribution," Pharmacological Research, 43(5):497-502 (2001).
Beaulac, C. et al., "Eradication of Mucoid *Pseudomonas aeruginosa* with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by *Pseudomonas aeruginosa*," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bermudez, L. E. et al., "Treatment of disseminated *Mycobacterium avium* complex infection of beige mice with liposome-encapsulated aminoglycosides," The Journal of Infectious Diseases, 161:1262-1268 (1999).

(56) References Cited

OTHER PUBLICATIONS

Bucke, W. E. et al., "Surface-modified amikacin-liposomes: organ distribution and interaction with plasma proteins," Journal of Drug Targeting, 5(2):99-108 (1997).
Bunderberg de Jong, H. G. et al., Koazevation (Entmischung in Kolloidalen Systemen), Koll, Zeitsch, 50(10):39-48 (1930).
Carlier, M. B. et al., "Inhibition of lysosomal phospholipases by aminoglycoside antibiotics: in vitro comparative studies," Antimicrobial Agents and Chemotherapy, 23(3):440-449 (1983).
Cantin, A. M. et al., "Aerosolized prolastin suppresses bacterial proliferation in a model of chronic *Pseudomonas aeruginosa* lung infection," Am. J. Respir. Crit. Care Med., 160:1130-1135 (1999).
Cash, H. A. et al., "A rat model of chronic respiratory infection with *Pseudomonas aeruginosa*," American Review of Respiratory Disease, 119(3):453-459 (1979).
Challoner, P. B. et al., "Gamma Scintigraphy Lung Deposition Comparison of TOBI in the PARI LC Plus Nebulizer and the Aerodose Inhaler," American Thoracic Society 97th International Conference, San Francisco, California, Aerogen, Inc. (2001).
Chambless, J. D. et al., "A three-dimensional computer model of four hypothetical mechanisms protecting biofilms from antimicrobials," Appl. Environ. Microbiol., 72(3):2005-2013 (2006).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Chmiel, J. F. et al., "State of the art: why do the lungs of patients with cystic fibrosis become infected and why can't they clear the infection?", Respiratory Research, 4:8-20 (2003).
Comis, R. L., "Carboplatin in the treatment of non-small cell lung cancer: a review," Oncology, 50(2):37-41 (1993).
Costerton, J. W. et al., "Bacterial biofilms: A common cause of persistent infections," Science, 284:1318-1322 (1999).
Couvreur, P. et al., "Liposomes and nanoparticles in the treatment of intracellular bacterial infections," Pharmaceutical Research, 8(9):1079-1085 (1991).
Cynamon, M. H. et al., "Liposome-Encapsulated-Amikacin Therapy of *Mycobacterium avium* Complex Infection in Geige Mice," Antimicrobial Agents and Chemotherapy, 33(8):1179-1183 (1989).
Damaso, D. et al., "Susceptibility of current clinical isolates of *Pseudomonas aeruginosa* and enteric gram-negative bacilli to amikacin and other aminoglycoside antibiotics," The Journal of Infectious Diseases, 134:S394-S390 (1976).
Dees, C. et al., "The mechanism of enhanced intraphagocytic killing of bacteria by liposomes containing antibiotics," Veterinary Immunology and Immunopathology, 24:135-146 (1990).
Demaeyer, P. et al., "Disposition of liposomal gentamicin following intrabronchial administration in rabbits," Journal Microencapsulation, 10(1):77-88 (1993).
Deol, P. et al., "Lung specific stealth liposomes: stability, biodistribution and toxicity of liposomal antitubular drugs in mice," Biochemica et Biophysica Acta, 1334:161-172 (1997).
Dong, C. et al., "Acacia-gelatin microencapsulated liposomes: preparation, stability and release of acetylsalicylic acid," Pharmaceutical Research, 10(1):141-146 (1993).
Doring, G. et al., "Antibiotic therapy against *Pseudomonas aeruginosa* in cystic fibrosis: a European consensus," Eur Respir J., 16(4):749-767 (2000).
Drenkard, E. et al., "*Pseudomonas* biofilm formation and antibiotic resistance are linked to phenotypic variation," Nature, 416:740-743 (2002).
Ehlers, S. et al., "Liposomal amikacin for treatment of *M. avium* Infections in clinically relevant experimental settings," Zbl. Bakt., 284:218-231 (1996).
Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).
Fountain, M. W. et al., "Treatment of *Brucella canis* and *Brucella abortus* in vitro and in vivo by stable plurilamellar vesicle-encapsulated aminoolycosides," The Journal of Infectious Diseases, 152(3):529-535 (1985).
Geller, D. E. et al., "Pharmacokinetics and bioavailability of aerosolized tobramycin in cystic fibrosis," Chest, 122(1):219-226 (2002).
Gibson, R. L. et al., "Pathophysiology and management of pulmonary infections in cystic fibrosis," American Journal of Respiratory and Critical Care Medicine, 168(8):918-951 (2003).
Gibson, R. L. et al., "Significant microbiological effect of inhaled tobramycin in young children with cystic fibrosis," American Journal of Respiratory and Critical Care Medicine, 167(6):841-849 (2003).
Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).
Gleiser, C. A. et al., "Pathology of experimental respiratory anthrax in *Macaca mulatta*," Brit. J. Exp. Path., 44:416-426 (1963).
Gonzales-Rothi, R. J. et al., "Liposomes and pulmonary alveolar macrophages: functional and morphologic interactions," Experimental Lung Research, 17:685-705 (1991).
Goss, C. H. et al., "Update on cystic fibrosis epidemiology," Current Opinion in Pulmonary Medicine, 10(6):510-514 (2004).
Gunther, A. et al., "Surfactant alteration and replacement in acute respiratory distress syndrome," Respiratory Research, 2(6): 353-364 (2001).
Hagwood, S. et al., "Structure and properties of surfactant protein B," Biochimica et Biophysica Acta., 1408:150-160 (1998).
Hansen, C. R. et al., "Long-term azithromycin treatment of cystic fibrosis patients with chronic *Pseudomonas aeruginosa* infection: an observational cohort study," Journal of Cystic Fibrosis, 4(1):35-40 (2005).
Hoffman, L. R. et al., "Aminoglycoside antibiotics induce bacterial biofilm formation," Nature, 436:1171-1175 (2005).
Howell, S. B., "Clinical applications of a novel sustained-release injectable drug delivery system: Depofoam Technology," Cancer Journal, 7:219-227 (2001).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).
Hung, O. R. et al., "Pharmacokinetics of inhaled liposome-encapsulated fentanyl," Anesthesiology, 83(2): 277-284 (1995).
Hunt, B. E. et al., "Macromolecular mechanisms of sputum inhibition of tobramycin activity," Antimicrobial Agents and Chemotherapy, 39(1):34-39 (1995).
Ikegami, M. et al., "Surfactant protein metabolism in vivo," Biochimica et Biophysica Acta, 1408:218-225 (1998).
Janoff, A. S. et al., "Unusual lipid structures selectively reduce the toxicity of amphotericin B," Proc. Nat. Acad. Sci. USA, 85:6122-6126 (1988).
Johansson, J., "Structure and properties of surfactant protein C," Biochimica et Biophysica Acta, 1408:161-172 (1998).
Katare, O. P. et al., "Enhanced in vivo Performance of LiposomalIndomethacin Derived From Effervescent Granule Based Proliposomes," J. Microencapsulation, 12(5):487-493 (1995).
Kesavalu, L. et al., "Differential effects of free and liposome encapsulated amikacin on the survival of *Mycobacterium avium* complex in mouse peritoneal macrophages," Tubercle, 71:215-218 (1990).
Kim, E. K. et al., "Pharmacokinetics of intravitreally injected liposomes encapsulated tobramycin in normal rabbits,"Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).
Knoch, M. et al., "The customised electronic nebuliser: a new category of liquid aerosol drug delivery systems," Expert Opin. Drug Deliv., 2(2):377-390 (2005).

(56) References Cited

OTHER PUBLICATIONS

Lagace, J. et al., "Liposome-encapsulated antibiotics: preparation, drug release and antimicrobial activity against *Pseudomona aeruginosa*," Journal Microencapsulation, 8(1) 53-61 (1991).
Landyshev, Y. S. et al., "Clinical and experimental aspects of liposomal hydrocortisone treatment of bronchial asthma," Ter. Arkh., 74(8):45-48 (2002).
Lass, J. S. et al., "New advances in aerosolised drug delivery: vibrating membrane nebuliser technology," Expert Opin Drug Deliv., 3(5):693-702 (2006).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Marier, J. F. et al., "Liposomal tobramycin against pulmonary infections of *Pseudomonas aeruginosa*: a pharmacokinetic and efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary *Burkholderia cepacia* infection," Antimicrobial Agents and Chemotherapy, 46(12):3776-3781 (2002).
Martini, W. Z. et al., "Lung surfactant kinetics in conscious pigs," Am J Physiol., 277(1 Pt 1): E187-E195 (1999).
McAllister, S. M. et al., "Antimicrobial properties of liposomal polymyxin B," Journal of Antimicrobial Chemotherapy, 43:203-210 (1999).
Mendelman, P. M. et al., "Aminoglycoside penetration, inactivation, and efficacy in cystic fibrosis sputum," American Review of Respiratory Disease, 132(4):761-765 (1985).
Mohanty, B. et al., "Systematic of alcohol-induced simple coacervation in aqueous gelatin solutions," Biomacromolecules, 4:1080-1086 (2003).
Morgan, J. R. et al., "Preparation and properties of liposome-associated gentamicin," Antimicrobial Agents and Chemotherapy, 17(4):544-548 (1980).
Myers, M. A. et al., "Pulmonary effects of chronic exposure to liposome aerosols in mice," Experimental Lung Research, 19:1-19 (1993).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium intracellulare* complex bacteremia in AIDS patients," Antimicrobial Agents and Chemotherapy, 37(9) 1869-1872 (1993).
Niven, R. W. et al., "Nebulization of liposomes. I. Effects of lipid composition," Pharmaceutical Research, 7(11):1127-1133 (1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
Omri, A. et al., "Incorporation, release and in-vitro antibacterial activity of liposomal aminoglycosides against *Pseudomonas aeruginosa*," Journal Antimicrobial Chemotherapy, 36:631-639 (1995).
Omri, A. et al., "Comparison of the Bactericidal Action of Amikacin, Netilmicin and Tobramtcin in Free and Liposomal Formulation against *Pseudomonas aeruginosa*," Chemotherapy, 42:170-176 (1996).
Omri, A. et al., "Pulmonary retention of free and liposome-encapsulated tobramycin after intratracheal administration in uninfected rats and rats infected with *Pseudomonas aeruginosa*," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery," Proc. Am. Thor. Soc., 1:338-344 (2004).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacal. Pharrn., 41:299-304 (1989).
Pilewski, J. M. et al., "Role of CFTR in airway disease," Physiological Reviews, 79(1):S215-S255 (1999).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by *Pseudomonas aeruginosa*," Journal of Antimicrobial Chemotherapy, 34:43-52 (1993).
Price, C. I. et al., "Liposome delivery of aminoglycosides in burn wounds," Surgery, Gynecolooy & Obstetrics, 174:414-418 (1992).
Price, C. I. et al., "Liposome encapsulation: a method for enhancing the effectiveness of local antibiotics," Surgery, 115(4):480-487 (1994).
Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O—C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Sabra, W. et al., "Physiological responses of pseudomonas aeruginosa PAO1 to oxidative stress in controlled microaerobic and aerobic cultures," Microbiology, 148:3195-3202 (2002).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).

(56) References Cited

OTHER PUBLICATIONS

Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Stott, P. W. et al., "Characterization of complex coacervates of some tricyclic antidepressants and evaluation of their potential for enhancing transdermal flux," Journal of Controlled Release, 41(3):215-227 (1996).
Sermet-Gaudelus, I. et al., "Nebulized antibiotics in cystic fibrosis," Paediatric Drugs, 4(7):455-467 (2002).
Shah, S. P. et al., "Liposomal amikacin dry powder inhaler: effect of fines on in vitro performance," AAPS PharmSciTech, 5(4):e65:1-7 (2004).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys. Bioeng., 9:467-508 (1980).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Thomas, D. A. et al., "Acute effects of liposome aerosol inhalation on pulmonary function in healthy human volunteers," Chest, 99(5):1268-1270 (1991).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of *Pseudomonas aeruginosa* to collagen type I," Antimicrobial Agents and Chemotherapy, 39(12):2645-2649 (1995).
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysica Acta, 1408:90-108 (1998).
Vidgren, M. et al., "A study of $^{99m}$ technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Wichert, B. V. et al., "Amikacin liposomes: characterization, aerosolization, and in vitro activity against *Mycobacterium avium-intracellulare* in alveolar macrophages," International Journal of Pharmaceutics, 78(2-3):227-235 (1992).
Wolff, R. K. et al., "Toxicologic testing of inhaled pharmaceutical aerosols," Critical Reviews in Toxicology, 23(4):343-369 (1993).
Worlitzsch, D. et al., "Effects of reduced mucus oxygen concentration in airway *Pseudomonas* infections of cystic fibrosis patients," J. Clin. Invest., 109:317-325 (2002).
Xiu, L. et al., "Drug Resistant Analysis of *Pseudomonas aeruginosa* in Patients with Mechanical Ventilation," Med. J. Chin. PLA, 27(6):544-545 (2002).
Yanagihara, K. et al., "Design of anti-bacterial drug and anti-Mycobacterial drug for drug delivery system," Current Pharmaceutical Design, 8:475-482 (2002).
Zeng, S. et al., "Intravitreal Pharmacokinetics of Liposome-encapsulated Amikacin in a Rabbit Model," Opthamology, 100:1640-1644 (1993).
Zhang, J. H. et al., "A Novel Method to Prepare Liposomes Containing Amikacin," Journal Microencapsulation, 16(4):511-516 (1999).
Office Action for U.S. Appl. No. 12/748,756, mailed Jan. 27, 2012.
Bilodeau, M. et al.,"Kanamycin aerosol therapy in 200 cases of bronchopulmonary suppurations," Can. Med. Assoc. J., 89:537-541 (1963) (with English Abstract).
Chan, C. H. S. et al., "Mycobacteria as a cause of infective exacerbation in bronchiectasis," Postgrad. Med. J., 68:896-899 (1992).
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Cremades, M. J. et al., "Repeated pulmonary infection by *Nocardia asteroides* complex in a patient with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).
Currie, D. C., "Nebulisers for bronchiectasis," Thorax, 52(Suppl. 2):572-574 (1997).
Dally, M. B. et al., "Ventilatory effects of aerosol gentamicin," Thorax, 33:54-56 (1978).
Dickie, K. J. et al., "Ventilatory effects of aerosolized kanamycin and polymyxin," Chest, 63(5):694-697 (1973).
El-Din, M. A. T. et al., "Nebulizer therapy with antibiotics in chronic suppurative lung disease," Journal of Aerosol Medicine, 7(4):345-350 (1994).
Eller, J. M. et al., "The therapy of bronchiectasis," Deutsche Medizinische Wochenschrift, 118(44):1608-1610 (1993).
Farber, J. E. et al., "The use of aerosol penicillin and streptomycin in bronchopulmonary infections," California Medicine, 73(3):214-217 (1950).
Finke, W., "Long-term antibiotic therapy in chronic bronchitis and infectious asthma. Control and prevention of bronchopulmonary disease." Antibiotics and Chemotherapy, 4(3):319-329 (1954).
Garcia, A. T., "Efficacy of amikacin sulfate in lower respiratory infections," Investigacion Medica Internacional, 9(3):235-240 (1982) (with English Abstract).
Goldman, J. M. et al., "Inhaled micronised gentamicin poweder: a new delivery system," Thorax, 45:939-940 (1990).
Graczyk, J. et al., "*Staphylococcal pneumonia*—analysis of material of patients treated in lung diseases hospital in years 1981-1994," Pneumonologia I Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Helbich, T. et al., "High-resolution computed tomography of the lung in young patients with cystic fibrosis," Radiologe, 33(3):142-146 (1993) (English Abstract).
Hewitt, W. L. et al., "Antibiotic therapy of abscess of the lung and bronchiectasis," California Medicine, 76(5):319-324 (1952).
Hubble, D., "Discussion on respiratory catarrh in children," Proceedings of the Royal Society of Medicine, 52(9):701-710 (1959).
Ikemoto, H. et al., "Susceptibility of bacteria isolated from the patients with lower respiratory tract infections to antibiotics," The Japanese Journal of Antibiotics, 42(11):2350-2353 (1989).

(56) References Cited

OTHER PUBLICATIONS

Ip, M. S. M. et al., "Bronchiectasis and related disorders," Respirology, 1:107-114 (1996).
Knox, K. et al., "Chronic bronchitis. An attempt to control chronic infection with *Haemophilus influenzae* by aerosol therapy," The Lancet, pp. 120-122 (1955).
Lin, H.-C. et al., "Inhaled gentamicin reduces airway neutrophil activity and mucus secretion in bronchiectasis," Am. J. Respir. Crit. Care Med., 155:2024-2029 (1997).
Marcotte, G. V. et al., "Chronic productive cough and bronchiectasis in a 40-year-old woman," Annals of Allergy, Asthma & Immunology, 78(6):559-564 (1997).
Mariotti, A. B. et al., "Aerosol therapy with tobramycin in exacerbations of chronic obstructive lung disease (7 cases)," 66(2):198-202 (1996) (with English Abstract).
Marwah, O. S. et al., "Bronchiectasis. How to identify, treat and prevent," Postgrad. Med., 97(2):149-150, 153-156, 159 (1995) (Abstract).
Mombelli, G. et al., "Anti-*Pseudomonas* activity in bronchial secretions of patients receiving amikacin or tobramycin as a continuous infusion," Antimicrobial Agents and Chemotherapy, 19(1):72-75 (1981).
Nakazawa, S. et al., "Studies on a new aminoglycoside antibiotic, amikacin (BB-K8) in pediatrics," The Japanese Journal of Antibiotics, 27(4):438-445 (1974).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of The Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Paradisi, F. et al, "Acute and chronic bronchopulmonary infections and aminoglycoside antibiotics," Chemioterapia Antimicrobica, 1(2):224-227 (1978).
Pines, A. et al., "Treatment of severe *Pseudomonas* infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Aerosol Antibiotic Therapy, 25:436-448 (1949).
Shima, K. et al., "A study of amikacin (BB-K8) on the clinical effects on the respiratory infection," Chemotherapy, 23(6):2128-2130 (1975) (with English Abstract).
Smith, A. L. et al., "Safety of aerosol tobramycin administration for 3 months to patients with cystic fibrosis," Pediatric Pulmonology, 7:265-271 (1989).
Takamoto, M. et al., "Imipenem/cilastatin sodium alone or combined with amikacin sulfate in respiratory infections," The Japanese Journal of Antibiotics, 47(9):1131-1144 (1994) (with English Abstract).
Terzano, C. et al., "Tobramycin aerosol: could the delivery system influence the particle size and deposition in the lower airways?" Recenti. Prog. Med., 89(5):245-249 (1998) (English Abstract).
Van Der Straeten, M. et al., "Amikacin in the treatment of gram-negative bronchopulmonary infections," The Journal of Infectious Diseases, 134:S391-S393 (1976).
Zlatanov, Zi. et al., "Gentamycin-pharmachim. Aerosol inhalation treatment of patients with chronic bronchitis," Medico Biologic Information 2, pp. 5-8 (1976).
Office Action for U.S. Appl. No. 13/664,181, mailed Aug. 22, 2013, 9 pages.
Office Action for U.S. Appl. No. 13/675,559, mailed Aug. 20, 2013, 9 pages.
Office Action for U.S. Appl. No. 13/675,587, mailed Aug. 21, 2013, 9 pages.
Office Action for U.S. Appl. No. 12/598,830, mailed Oct. 23, 2012.
Office Action for Chinese Patent Application No. 200980140740.2, dated Jun. 4, 2013.
Office Action for New Zealand Patent Application No. 592217, mailed Feb. 5, 2013.
Search Report and Written Opinion for Singapore Application No. 201102419-7, mailed Sep. 7, 2012.
First Examination Report for New Zealand Patent Application No. 606383, dated Feb. 5, 2013.
Office Action for Israel Application No. 168279, dated Jun. 6, 2012.
Office Action for Korean Patent Application No. 10-2005-7007679, dated Dec. 26, 2012.
International Preliminary Report on Patentability for International Application No. PCT/US2003/034240, mailed May 6, 2013.
Office Action for Japanese Patent Application No. 2011-001318, mailed Feb. 12, 2013.
Office Action for Mexican Patent Application No. MX/a/2010/000195, mailed Oct. 2, 2012.
Office Action for Canadian Patent Application No. 2,614,764, dated Nov. 14, 2012.
Third Office Action for Chinese Patent Application No. 200680034397.X, dated Mar. 12, 2012.
Fourth Office Action for Chinese Patent Application No. 200680034397.X, dated Dec. 4, 2012.
Office Action for Columbian Patent Application No. 08016117, dated Jun. 26, 2012.
Office Action for Columbian Patent Application No. 08016117, dated Jan. 14, 2013.
Office Action for Costa Rican Patent Application No. 9736, dated Apr. 22, 2013.
Office Action for European Application No. 06787716.7, dated Oct. 26, 2012.
Office Action for Israel Patent Application No. 188406, dated Jan. 6, 2013.
Office Action for Korean Patent Application No. 10-2008-7002031, dated Dec. 21, 2012.
Office Action for Canadian Patent Application No. 2,646,255, dated Feb. 4, 2013.
Supplementary European Search Report for European Application No. 07754853, mailed Jan. 16, 2013.
Office Action for Japanese Patent Application No. 2009-504281, dated Sep. 4, 2012.
Office Action for U.S. Appl. No. 12/748,756, mailed Aug. 23, 2012.
Office Action for Canadian Patent Application No. 2,631,872, dated Dec. 7, 2012.
Supplementary European Search Report for European Application No. 06847502, mailed Dec. 5, 2012.
Office Action for U.S. Appl. No. 13/527,213, mailed Mar. 11, 2013.
Office Action for U.S. Appl. No. 13/664,181, mailed Feb. 12, 2013.
Office Action for U.S. Appl. No. 13/666,420, mailed Mar. 5, 2013.
Office Action for U.S. Appl. No. 13/675,559, mailed Mar. 19, 2013.
Office Action for U.S. Appl. No. 13/675,587, mailed Apr. 4, 2013.
Supplementary European Search Report and Written Opinion for European Application No. 07754936, mailed Jan. 18, 2013.
Office Action for Japanese Patent Application No. 2009-504301, dated Sep. 4, 2012.
Clay. M. M. et al., "Assessment of jet nebulisers for lung aerosol therapy," Lancet, 2:592-594 (1983).
Deamer, D. W. et al., "Liposome Preparation: Methods and Mechanisms," Chapter 1 in: Liposomes, Ostro, M. J. (ed.), Marcel Dekker, Inc., New York (1983), 27 pages.
Hess, D. et al., "Medication nebulizer performance. Effects of diluent volume, nebulizer flow, and nebulizer brand," Chest, 110:498-505 (1996).
Hess, D. R., "Nebulizers: Principles and Performance," Respiratory Care, 45(6):609-622 (2000).
Ishii, F. et al., "Procedure for Preparation of Lipid Vesicles (Liposomes) Using the Coacervation (Phase Separation) Technique," Langmuir, 11(2):483-486 (1995).

(56) References Cited

OTHER PUBLICATIONS

Wang, W. et al., "Research progress in pulmonary administration of liposome," Journal of Shenyang Pharmaceutical University, 17(3):226-229 (2000).
Bangham, A. D. et al., "Diffusion of univalent ions across the lamellae of swollen phospholipids," J. Mol. Biol., 13:238-252 (1965).
Papahadjopoulos, D. et al., "Phospholipid model membrames. I. Structrual characteristics of hydrated liquid crystals," Biochimica et Biophysica Acta., 135:624-638 (1967).
Office Action for U.S. Appl. No. 12/598,830, mailed Apr. 18, 2014.
Office Action for U.S. Appl. No. 12/250,412, mailed Mar. 24, 2014.
Office Action for Chilean Application No. 814-2011, dated Apr. 8, 2014.
Office Action for Chinese Patent Application No. 200980140740.2, dated Mar. 5, 2014.
Office Action for Israel Patent Application No. 212268, dated Dec. 9, 2013.
Office Action for Japanese Patent Application No. 2011-532180, dated May 1, 2014.
Office Action for Japanese Patent Application No. 2011-532180, dated Jan. 23, 2014.
Office Action for Russia Patent Application No. 2011119018, dated Mar. 5, 2014.
Office Action for Ukraine Patent Application No. 201105955, dated Jun. 7, 2013.
Office Action for Israel Patent Application No. 168279, dated Mar. 19, 2014.
Official Action for Korean Patent Application No. 10-2013-7010499, dated Sep. 2, 2013.
Office Action for Mexican Patent Application No. MX/a/2010/000195, mailed May 31, 2013.
Office Action for Indian Patent Application No. 353/DELNP/2008, dated Jul. 26, 2013.
Office Action for Japanese Patent Application No. 2008-522895, dated Aug. 27, 2013.
Office Action for Chinese Application No. 201310149581.0, mailed Apr. 21, 2014.
Office Action for European Application No. 07754853, mailed Feb. 3, 2014.
Office Action for Japanese Patent Application No. 2009-504281, mailed Nov. 1, 2013.
Office Action for Korean Patent Application No. 10-2013-7031379, dated Feb. 25, 2014.
Office Action for Japanese Application No. 2013-146934, mailed May 26, 2014.
Office Action for Korean Application No. 10-2014-7005780, Jun. 26, 2014.
Office Action for U.S. Appl. No. 12/424,177, mailed Jul. 21, 2014.
Office Action for U.S. Appl. No. 12/424,177, mailed Dec. 24, 2013.
European Search Report for European Patent Application No. 13175824, mailed Sep. 16, 2013.
Office Action for Japanese Application No. 2013-167610, dated Aug. 8, 2014.
Office Action for U.S. Appl. No. 12/983,659, mailed Dec. 2, 2013.
Office Action for U.S. Appl. No. 12/983,659, mailed Jun. 17, 2014.
Office Action for European Patent Application No. 06847502.9, mailed Oct. 14, 2013.
Office Action for European Patent Application No. 06847502.9, mailed Jul. 16, 2014.
Office Action for U.S. Appl. No. 14/080,922, mailed Jun. 12, 2014.
Office Action for Japanese Patent Application No. 2009-504301, mailed Oct. 31, 2013.
Office Action for U.S. Appl. No. 11/696,343, mailed May 23, 2014.
International Search Report and Written Opinion for International Application No. PCT/US2013/042113, mailed Sep. 4, 2013.
Dequin, P. F. et al., "Urinary excretion reflects lung deposition of aminoglycoside aerosols in cystic fibrosis," Eur. Respir. J., 18(2):316-322 (2001).
Meers, P. et al., "Biofilm penetration, triggered release and in vivo activity of inhaled liposomal amikacin in chronic *Pseudomonas aeruginosa* lung infections," Journal of Antimicrobial Chemotherapy, 61(4):859-868 (2008).
Schiffelers, R. et al., "Liposome-encapsulated aminoglycosides in pre-clinical and clinical studies," Journal of Antimicrobial Chemotherapy, 48:333-344 (2001).
Office Action for U.S. Appl. No. 12/598,830, mailed Nov. 28, 2014.
Office Action for Chilean Application No. 814-2011, dated Nov. 4, 2014.
Office Action for Indonesian Application No. W00201101412, dated Feb. 28, 2014.
Office Action for Philippine Application No. 12011500726, mailed Apr. 24, 2014.
Second Written Opinion for Singapore Application No. 201102419-7, mailed Sep. 4, 2014.
Office Action for Chinese Application No. 201310149581.0, mailed Oct. 17, 2014.
Office Action for Israel Application No. 216401, dated May 27, 2014.
Office Action for Canadian Application No. 2,838,111, dated Nov. 27, 2014.
International Preliminary Report on Patentability for International Application No. PCT/US2013/042113, dated Nov. 25, 2014, 9 pages.
Del Porto, P. et al., "Dysfunctional CFTR alters the bactericidal activity of human macrophages against Pseudomonas aeruginosa," PLoS ONE, 6(5):e19970 (2011).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Office Action for Japanese Application No. 2014-075240, dated Mar. 9, 2015, 2 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
Office Action for Canadian Application No. 2,838,108, mailed Jan. 6, 2015, 3 pages.
Office Action for Canadian Application No. 2,853,611, mailed Mar. 5, 2015, 3 pages.
Office Action for Japanese Application No. 2014-040222, dated Feb. 10, 2015, 1 page.
European Search Report for European Application No. 14183066.1, mailed Dec. 16, 2014, 11 pages.
Office Action for U.S. Appl. No. 11/696,343, mailed Feb. 3, 2015, 11 pages.
Cooksey, R. C. et al., "Antimicrobial susceptibility patterns of *Streptococcus pneumoniae*," Antimicrobial Agents and Chemotherapy, 13(4):645-648 (1978).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Office Action for U.S. Appl. No. 14/080,922, mailed Mar. 3, 2015, 16 pages.

| | | | | | |
|---|---|---|---|---|---|
| 280 mg Arikace | -0.141 | -1.391 | -1.236 | -0.816 | -0.480 |
| 560 mg Arikace | -0.993 | -1.263 | -2.138 | -1.163 | -1.788 |
| Placebo | -0.033 | -0.600 | -0.510 | -0.772 | -0.449 |

METHOD OF TREATING PULMONARY DISORDERS WITH LIPOSOMAL AMIKACIN FORMULATIONS

RELATED APPLICATIONS

This application claims priority from U.S. Provisional Application No. 61/489,940, filed May 25, 2011, and is a continuation in part of U.S. application Ser. No. 12/250,412, filed on Oct. 13, 2008, which is a continuation in part of International Application No. PCT/US08/062868, filed on May 7, 2008, which claims priority from U.S. Provisional Application No. 60/916,342, filed on May 7, 2007, all of which are hereby incorporated by reference in their entirety.

BACKGROUND OF THE INVENTION

Cystic fibrosis (CF), also called mucoviscidosis, is an autosomal, recessive, hereditary disease of the exocrine glands. It affects the lungs, sweat glands and the digestive system, causing chronic respiratory and digestive problems. It is caused by mutations in the cystic fibrosis transmembrane conductance regulator (CFTR) protein. It is the most common fatal autosomal recessive diseases amongst Caucasions.

The first manifestation of CF is sometimes meconium ileus, occurring in 16% of infants who develop CF. Other symptoms of CF manifest during early childhood. Both lungs and pancreas produce abnormally viscous mucus. This mucus begins to build up and starts to clog the opening to the pancreas and the lungs. Pulmonary problems start from the constant presence of thick, sticky mucus and are one of the most serious complications of CF. The mucus in the lungs can become a growth medium for bacteria, resulting in chronic respiratory infections and eventual permanent damage to the lung tissue. During the end stage of CF, the patient experiences increased chest congestion, activity intolerance, increased crackles, and increased cough, which often contains sputum mixed with blood (hemoptysis) due to the bronchiole bleeding from the lung arteries. A chronic and loose sounding cough is common in people with CF. These thick secretions also obstruct the pancreas, preventing digestive enzymes from reaching the intestines to help break down and absorb food. Frequent and foul smelling stools are often an early sign of CF along with fatty oil that is visible in the stool. This can compromise growth and overall nutrition if proper treatment to aid digestion is not utilized early in life. As lung function deteriorates, CF patients can develop pulmonary hypertension, chronic bronchitis, and chronic dilation of the bronchioles (bronchiectasis). Lung abscess are very common. Death usually occurs from severe infection, pneumonia, or heart failure.

Cystic fibrosis is exclusively heritable as both parents must carry the recessive genes for a child to acquire the disease. At the genetic level, cystic fibrosis is most often the result of an in-frame deletion of three base pairs in the DNA. Cystic fibrosis results from the production of an abnormal form of a protein called cystic fibrosis transmembrane conductance regulator (CFTR). CFTR functions in transporting chloride ions across epithelial cells found in the lung and intestinal tract. In CF patients, CFTR does not function properly, causing accumulation of ions inside epithelial cells. Since water follows ions by osmosis, this results in water depletion and viscous mucus on the surface of alveoli. The most common CFTR protein abnormality is a mutation termed $\Delta F508$, which is characterized by the 3-bp deletion of the DNA base-pair sequence at chromosome location 7q31.1-31.2 that codes for the amino acid, phenylalanine.

In addition to pulmonary infections, most people with CF also have problems with digestion, particularly the digestion of fats. This leads to malabsorption and difficulty gaining and maintaining weight, which in turn affects overall health. This is due to the abnormally sticky mucus that blocks the release of digestive enzymes from the pancreas. Pancreatic insufficiency is treated with supplemental enzymes. Usually water-miscible forms of the fat-soluble vitamins A, D, E, and K are required as the decreased fat absorption can lead to deficiencies of these vitamins.

CF patients also have an increased incidence of diabetes mellitus because of the pancreatic blockage. The chronic blocking causes the Islets of Langerhans to degrade over time and decrease insulin production, causing hyperglycemia. There is also evidence that patients with CF become more resistant to the insulin that is produced, this can be triggered by infections or treatment with corticosteroids. Diabetes in CF patients is commonly referred to as CFRD, cystic fibrosis related diabetes. A typical diabetic diet is not feasible and therefore insulin doses are instead adjusted to fit the typical high-calorie/high-fat CF diet.

Many CF patients, to some degree, experience the widening of the tips of their fingers, known as "clubbing". The condition affects fingers and toes, and results in the tip of the digit being round and enlarged. This can also be seen in people with COPD or severe heart disease. Since people with CF are prone to poor absorption of nutrients, osteoporosis can occur in early adulthood due to low bone density. It is important for people with CF to have regular dual energy X-ray absorptiometry (DEXA) scans to measure bone density and begin treatment if needed. When diagnosed early, treatment can help prevent more serious complications.

Some CF patients have hearing loss as a side effect of long-term use of the -mycin/-micin group of drugs, such as Tobramycin, which is used to combat lung infections. Although this side-effect is well-known and understood, these particular antibiotics are of high value in the treatment of CF patients, and often the hearing loss must be considered a necessary trade-off in order to preserve life and health. CF occurs primarily in individuals of central and western European origin. In the United States, the median age at death has increased from 8.4 years of age in 1969 to 14.3 years of age in 1998. The mean age of death has increased from 14 years in 1969 to 32.4 years of age in 2003 (Cystic Fibrosis Foundation). A major contributor to the significant increase in life expectancy is improved antibiotic treatment of chronic respiratory tract infections in CF subjects (Goss and Rosenfeld 2004) as well as improved nutrition and earlier diagnosis.

A major factor in the respiratory health of CF subjects is acquisition of chronic *Pseudomonas aeruginosa* infections. The infection rate with *P. aeruginosa* increases with age and by age 18 years, 80% of CF subjects in the U.S. are infected. The difficulties treating this infection are multifactorial, including poor penetration of antibiotics into sites of infection including mucus plugs, inactivation of antibiotics by CF sputum, growth of bacteria in a biofilm, changes in phenotype including conversion to a mucoid form of *P. aeruginosa*, and emergence of multi-drug resistance (Chmiel and Davis 2003; Gibson, Burns et al. 2003). The cornerstone of pulmonary therapy is optimizing treatment of *P. aeruginosa* as infection with this pathogen is associated with a poor clinical outcome (Doring, Conway et al. 2000; Chmiel and Davis 2003; Gibson, Burns et al. 2003; Gibson, Emerson et al. 2003).

One of the current approaches to management of chronic *P. aeruginosa* infection in humans with CF includes the use of suppressive therapy with inhaled tobramycin (TOBI®). Inhaled tobramycin, 300 mg, administered twice a day for cycles of 28 days followed by 28 days off drug has been shown to reduce *P. aeruginosa* colony counts, increase $FEV_1\%$ predicted, reduce hospitalizations, and decrease antibiotic use (Ramsey, Pepe et al. 1999). Nevertheless, patients have to be dosed twice a day for approximately 15-20 minute inhalation periods per dose.

Daily chest physiotherapy and aerosol breathing treatments are very commonly prescribed for CF patients. Typical physical therapy involves manual chest percussion (pounding), positive pressure techniques and/devices or possibly using a device such as the ThAIRapy Vest or the Intrapulmonary Percussive Ventilator (IPV) to achieve the same effect: loosening of the thick mucus. Aerosolized medicines commonly given include albuterol, ipratropium bromide and Pulmozyme to loosen secretions and decrease inflammation. It was found that CFers who surf were healthier; consequently, some hospitals use a nebulized 6%-10% Saline solution on those CFers who do not have asthma to loosen the secretions. Inhaled aminoglycoside antibiotics are sometimes given to fight infections. A number of pharmacological agents that help mucosal clearance are being used. N-acetylcysteine that solubilizes mucus glycoprotein, however, has not proved to be significantly effective. Recombinant human DNAse decreases the viscosity of sputum by degrading the concentrated amount of DNA in the sputum of CF patients. DNAse treatment has been beneficial in increasing airflow during short-term use, and has also prolonged the interval between episodes of pulmonary exacerbations.

CF patients are typically hospitalized somewhat regularly, often every 6 months depending on the severity of the case. Patients often have intravenous antibiotics through a PICC line, Central Line, or Port-a-Caths.

Cystic fibrosis can also lead to bronchiectasis. Bronchiectasis is an abnormal stretching and enlarging of the respiratory passages caused by mucus blockage. When the body is unable to get rid of mucus, mucus becomes stuck and accumulates in the airways. The blockage and accompanying infection cause inflammation, leading to the weakening and widening of the passages. The weakened passages can become scarred and deformed, allowing more mucus and bacteria to accumulate, resulting in a cycle of infection and blocked airways. Bronchiectasis is a disease that causes localized, irreversible dilatation of part of the bronchial tree. Involved bronchi are dilated, inflamed, and easily collapsible, resulting in airflow obstruction and impaired clearance of secretions. Bronchiectasis is associated with a wide range of disorders, but it usually results from necrotizing bacterial infections, such as infections caused by the *Staphylococcus* or *Klebsiella* species or *Bordatella pertussis*.

Bronchiectasis is one of the chronic obstructive pulmonary diseases (COPD) and it can be complicated by emphysema and bronchitis. The disease is commonly misdiagnosed as asthma or pneumonia. Bronchiectasis can develop at any age, begins most often in childhood, but symptoms may not be apparent until much later. Bronchiectasis can occur as part of a birth defect, such as primary ciliary dyskinesia or cystic fibrosis. About 50% of all cases of bronchiectasis in the U.S. result from cystic fibrosis. It can also develop after birth as a result of injury or other diseases, like tuberculosis, pneumonia and influenza.

Dilation of the bronchial walls results in airflow obstruction and impaired clearance of secretions because the dilated areas interrupt normal air pressure of the bronchial tubes, causing sputum to pool inside the dilated areas instead of being pushed upward. The pooled sputum provides an environment conducive to the growth of infectious pathogens, and these areas of the lungs are thus very vulnerable to infection. The more infections that the lungs experience, the more damaged the lung tissue and alveoli become. When this happens, the bronchial tubes become more inelastic and dilated, which creates a perpetual, destructive cycle within this disease.

There are three types of bronchiectasis, varying by level of severity. Fusiform (cylindrical) bronchiectasis (the most common type) refers to mildly inflamed bronchi that fail to taper distally. In varicose bronchiectasis, the bronchial walls appear beaded, because areas of dilation are mixed with areas of constriction. Saccular (cystic) bronchiectasis is characterized by severe, irreversible ballooning of the bronchi peripherally, with or without air-fluid levels. Chronic productive cough is prominent, occurring in up to 90% of patients with bronchiectasis. Sputum is produced on a daily basis in 76% of patients.

In addition to CF, other genetic causes or contributing factors to bronchiectasisis include Kartagener syndrome, Young's syndrome, alpha 1-antitrypsin deficiency, and Primary immunodeficiencies. Acquired bronchiectasis occurs more frequently, with one of the biggest causes being tuberculosis. A especially common cause of the disease in children is Acquired Immunodeficiency Syndrome, stemming from the human immunodeficiency virus. Other causes of bronchiectasis include respiratory infections, obstructions, inhalation and aspiration of ammonia, and other toxic gases, pulmonary aspiration, alcoholism, heroin use and allergies. Cigarette smoking may also contribute to bronchiectasis.

The diagnosis of bronchiectasis is based on the review of clinical history and characteristic patterns in high-resolution CT scan findings. Such patterns include "tree-in-bud" abnormalities and cysts with definable borders. Bronchiectasis may also be diagnosed without CT scan confirmation if clinical history clearly demonstrates frequent, respiratory infections, as well confirmation of an underlying problem via blood work and sputum culture samples.

Symptoms include coughing (worsened when lying down), shortness of breath, abnormal chest sounds, weakness, weight loss, and fatigue. With infections the mucus may be discolored, foul smelling and may contain blood. Symptom severity varies widely from patient to patient and occasionally, a patient is asymptomatic.

Treatment of bronchiectasis is aimed at controlling infections and bronchial secretions, relieving airway obstruction, and preventing complications. This includes prolonged usage of antibiotics to prevent detrimental infections, as well as eliminating accumulated fluid with postural drainage and chest physiotherapy. Surgery may also be used to treat localized bronchiectasis, removing obstructions that could cause progression of the disease.

Inhaled steroid therapy that is consistently adhered to can reduce sputum production and decrease airway constriction over a period of time will prevent progression of bronchiectasis. One commonly used therapy is beclometasone dipropionate, also used in asthma treatment. Use of inhalers such as Albuterol (Salbutamol), Fluticasone (Flovent/Flixotide) and Ipratropium (Atrovent) may help reduce likelihood of infection by clearing the airways and decreasing inflammation.

Mannitol dry inhalation powder, under the name Bronchitol, has been approved by the FDA for use in Cystic Fibrosis patients with Bronchiectasis. The original orphan drug indication approved in February 2005 allowed its use for the treatment of bronchiectasis. The original approval was based on the results of phase 2 clinical studies showing the product to be safe, well-tolerated, and effective for stimulating mucus hydration/clearance, thereby improving quality of life in patients with chronic obstructive lung diseases like Bronchiectasis. Long-term studies are underway as of 2007 to ensure the safety and effectiveness of the treatment.

Bronchiectasis patients are often given antibiotics for infection and bronchodilator medicines to open passages. Sometimes antibiotics are prescribed for a long period to prevent recurring infections, especially in people who have cystic fibrosis. There are also physical therapy techniques to help clear mucus. Lung transplants are also an option for severe cases. Fatalities are uncommon but may result from massive hemorrhage. If lung infections are treated immediately, bronchiectasis is less likely to develop.

Pneumonia is an illness of the lungs and respiratory system in which the alveoli (microscopic air-filled sacs of the lung responsible for absorbing oxygen from the atmosphere) become inflamed and flooded with fluid. Pneumonia can result from a variety of causes, including infection with bacteria, viruses, fungi, or parasites, and chemical or physical injury to the lungs. Typical symptoms associated with pneumonia include cough, chest pain, fever, and difficulty in breathing. Diagnostic tools include x-rays and examination of the sputum.

Therefore, there is a need for therapies to treat pulmonary disorders, including CF, pulmonary infections, COPD, bronchiectasis and others. Additionally, there is a need to improve lung function in patients having such disorders.

SUMMARY OF THE INVENTION

The present invention relates in part to a method of treating a pulmonary disorder in a patient comprising administering to the patient an effective dose of a nebulized liposomal amikacin formulation for at least one treatment cycle, wherein:
the treatment cycle comprises an administration period of 15 to 75 days, followed by an off period of 15 to 75 days; and the effective dose comprises 100 to 2500 mg of amikacin daily during the administration period.

In some embodiments, the treatment cycle is administered to the patient at least twice. In some embodiments, the administration period is 15 to 35 days, or 20 to 35 days. In other embodiments, the administration period is about 28 days. In some embodiments, the off period is 15 to 35 days, or 20 to 35 days. In other embodiments, the off period is about 28 days. In still other embodiments, the off period is of 25 to 75 days, 35 to 75 days, or 45 to 75 days. In other embodiments, the off period is about 56 days.

In some embodiments, the administration period is about 28 days and the off period is about 28 days, while in other embodiments, the administration period is about 28 days and the off period is about 56 days.

In some embodiments, the effective dose comprises 250 to 1,500 mg of amikacin, 250 to 1000 mg of amikacin, or about 280 to about 560 mg of amikacin. In other embodiments, the effective dose is about 280 or about 560 mg of amikacin.

In some embodiments, the pulmonary disorder is selected from the group consisting of chronic obstructive pulmonary disease, bronchiectasis, pulmonary infection, cystic fibrosis, alpha-1-antitrypsin enzyme deficiency and a combination thereof. In other embodiments, the pulmonary condition is a bacterial pulmonary infection, such as a *P. aeruginosa* infection. In some embodiments, the pulmonary condition is bronchiectasis.

In some embodiments, the patient has a serum $C_{max}$ of amikacin of less than about 10 mcg/mL during the administration period. In other embodiments, the patient has a sputum $C_{max}$ of amikacin of at least 1000 mcg per gram of sputum either during the administration, for at least 15 days after the administration.

In some embodiments, the patient has a reduction in $\log_{10}$ CFU of the bacterial infection in the lungs of at least 0.5 for at least 15 days after the administration period ends. In other embodiments, the reduction in the $\log_{10}$ CFU is at least 1.0.

In some embodiments, the patient experiences an improvement in lung function for at least 15 days after the administration period ends. For example, the patient may experience an increase in $FEV_1$, an increase in blood oxygen saturation, or both. In some embodiments, the patient has an $FEV_1$ that is increased by at least 5% over the $FEV_1$ prior to the treatment cycle. In other embodiments, $FEV_1$ is increased by 5 to 50%. In other embodiments, $FEV_1$ is increased by 25 to 500 mL over $FEV_1$ prior to the treatment cycle. In some embodiments, blood oxygen saturation is increased by at least 1% over oxygen saturation prior to the treatment cycle.

In some embodiments, the length of time to a pulmonary exacerbation is at least 20 days from the last day of administration. In other embodiments, the length of time to a rescue treatment is at least 25 days from the last day of the administration.

In some embodiments, the liposomal amikacin formulation comprises a lipid selected from the group consisting of egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidyl-ethanolamine (DOPE), palmitoylstearoylphosphatidyl-choline (PSPC), palmitoylstearolphosphatidylglycerol (PSPG), mono-oleoyl-phosphatidylethanolamine (MOPE), cholesterol, ergosterol, lanosterol, tocopherol, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethyl ammonium chloride (DOTMA), 1,2-bis(oleoyloxy)-3-(trimethylammonio)propane (DOTAP), phosphatidyl-glycerols (PGs), phosphatidic acids (PAs), phosphatidylinositols (PIs), phosphatidyl serines (PSs), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphospatidylinositol (DSPI), dimyri stoylphosphatidylserine (DMPS), dipalmitoylphosphatidylserine (DPPS), distearoylphosphatidylserine (DSPS), and mixtures thereof. In other embodiments, the liposomal amikacin formulation comprises a phospholipid and a sterol, such as DPPC and cholesterol. In other embodiments, the liposomal amikacin formulation comprises DPPC and cholesterol in about a 2 to 1 ratio by weight. In some embodiments, the liposomal amikacin formulation has a lipid to drug ratio of about 0.5 to about 1.0, about 0.5 to 0.7, or about 0.6 by weight.

DETAILED DESCRIPTION OF THE INVENTION

I. Definitions

Figure 1:
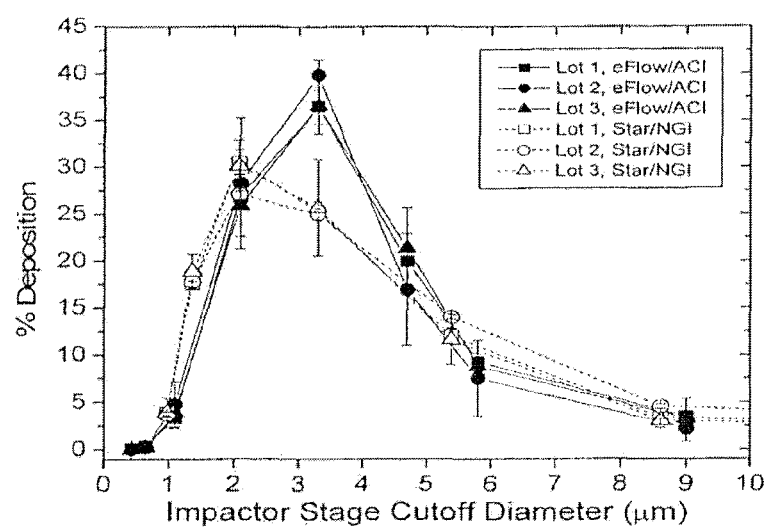
FIG. 1 depicts mass distribution of Liposomal Amikacin nebulizate collected on impactor stages as a function of cutoff diameter. The three Liposomal Amikacin lots of Table 15 legend (designated as 1, 2, and 3) were used with the eFlow nebulizer and ACI system (solid symbols) or the LC Star nebulizer and NGI system (open symbols).

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "pulmonary disorder" refers to any disease, ailment, or other unhealthy condition related to the respiratory tract of a subject, particularly the lungs of a subject. Generally pulmonary distress results in difficulty of breathing.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The terms "therapeutically effective dose" and "therapeutically effective amount" refer to that amount of a compound that results in prevention or amelioration of symptoms in a patient or a desired biological outcome, e.g., improved clinical signs, delayed onset of disease, reduced levels of bacteria, etc.

The term "$FEV_1$" is well known in the art as a measure of lung function, and refers to the forced expiratory volume in one second. The $FEV_1$ values used herein are measured in mLs, and also in terms of percent change from baseline, e.g., a change from pre-treatment values.

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

II. Liposomal Amikacin

Liposomal amikacin formulations useful in the presently disclosed methods can be prepared as described, for example, in U.S. Publication No. 20060073198 or 20080089927, both of which are hereby incorporated by reference. Generally, amikacin is used in the form of a pharmaceutically acceptable salt, for example the sulfate salt of amikacin.

The lipids used in the compositions of the present invention can be synthetic, semi-synthetic or naturally-occurring lipids, including phospholipids, tocopherols, steroids, fatty acids, glycoproteins such as albumin, anionic lipids and cationic lipids. The lipids may be anionic, cationic, or neutral. In one embodiment, the lipid formulation is substantially free of anionic lipids, substantially free of cationic lipids, or both. In one embodiment, the lipid formulation comprises only neutral lipids. In another embodiment, the lipid formulation is free of anionic lipids or cationic lipids or both. In another embodiment, the lipid is a phospholipid. Phospholipids include egg phosphatidyl choline (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidyl choline (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC). Other examples include dimyristoylphosphatidylcholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), driacylglycerol, diacylglycerol, seranide, sphingosine, sphingomyelin and single acylated phospholipids like mono-oleoyl-phosphatidylethanol amine (MOPE).

The lipids used can include ammonium salts of fatty acids, phospholipids and glycerides, phosphatidylglycerols (PGs), phosphatidic acids (PAs), phosphotidylcholines (PCs), phosphatidylinositols (PIs) and the phosphatidylserines (PSs). The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9(Z)-octadecenyloxy)-prop-1-yl-N,N,N-trimethylammonium chloride (DOTMA) and 1,2-bis(oleoyloxy)-3-(trimethylammonio)propane (DOTAP). Examples of PGs, PAs, PIs, PCs and PSs include DMPG, DPPG, DSPG, DMPA, DPPA, DSPA, DMPI, DPPI, DSPI, DMPS, DPPS and DSPS, DSPC, DPPG, DMPC, DOPC, egg PC.

In another embodiment, the liposome comprises a lipid selected from the group consisting of phosphatidyl cholines (PCs), phosphatidyl-glycerols (PGs), phosphatidic acids (PAs), phosphatidylinositols (PIs), and phosphatidyl serines (PSs).

In another embodiment, the lipid is selected from the group consisting of: egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidyl choline (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidyl-ethanolamine (DOPE), palmitoylstearoylphosphatidyl-choline (PSPC), palmitoylstearolphosphatidylglycerol (PSPG), mono-oleoyl-phosphatidylethanolamine (MOPE), tocopherol, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis (oleoyloxy)-3-(trimethylammonio)propane (DOTAP), distearoylphosphatidylglycerol (DSPG), dimyristoylphosphatidylacid (DMPA), dipalmitoylphosphatidylacid (DPPA), di stearoylphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), and mixtures thereof.

In another embodiment, the liposome comprises a phosphatidyl choline. The phosphatidyl choline may be unsaturated, such as DOPC or POPC, or saturated, such as DPPC. In another embodiment, the liposome does not include a sterol. In one embodiment, the liposome consists essentially of a phosphatidyl choline and a sterol. In another embodiment, the liposome consists essentially of DPPC and cholesterol.

Liposomes or lipid antiinfective formulations composed of phosphatidylcholines, such as DPPC, aid in the uptake by the cells in the lung such as the alveolar macrophages and helps to sustain release of the antiinfective agent in the lung (Gonzales-Rothi et al. (1991)). The negatively charged lipids such as the PGs, PAs, PSs and PIs, in addition to reducing particle aggregation, can play a role in the sustained release characteristics of the inhalation formulation as well as in the transport of the formulation across the lung (transcytosis) for systemic uptake.

While not being bound by any particular theory, it is believed that when the lipid comprises a neutral lipid, and does not comprise a negatively charged or positively charged phospholipid, the liposomal formulation has improved uptake by the lungs. For example, the liposome my have improved penetration into a biofilm or mucus layer when the lipid comprises only neutral lipids. Exemplary neutral lipids include the aforementioned phosphatidylcholines, such as DPPC and sterols, such as cholesterol.

IV. Methods of Treatment

The present invention is directed to methods of treating a pulmonary condition in a subject need thereof comprising administering to the subject and effective amount of any one of the aforementioned liposomal antibiotic formulations. In some embodiments, the pulmonary condition is a bacterial infection. In some embodiments, the method comprises administering to a patient in need thereof an effective amount of a liposomal amikacin formulation (also referred to herein as "liposomal amikacin") by inhalation daily. In some embodiments, the administration by inhalation comprises nebulizing the liposomal formulation.

In some embodiments, the liposomal amikacin formulation is administered daily for a period of time, followed by second period of time (an "off" period) wherein no liposomal formulation is administered. For example, in some embodiments, the method of treating a pulmonary disorder comprises administering to the patient an effective dose of a nebulized liposomal amikacin formulation for at least one treatment cycle, wherein:
  the treatment cycle comprises an administration period of 15 to 75 days, followed by an off period of 15 to 75 days; and the effective dose comprises 100 to 2500 mg of amikacin daily during the administration period.

In some embodiments, the aforementioned treatment cycle is administered to the patient at least twice. In other embodiments, the treatment cycle may be administered 3, 4, 5, 6, or more times.

During the administration period, liposomal amikacin is administered daily. In some embodiments, liposomal amikacin can be administered every other day or every third day during the administration period. As explained above, the administration period can be 15 to 75 days. In some embodiments, the administration period is 15 to 35 days, or 20 to 35 days. In other embodiments, the administration period is 20 to 30 days, 25 to 35 days or 25 to 30 days. In other embodiments, the administration period is about 25, 26, 27, 28, 29 or 30 days. In another embodiment, the administration period is about 28 days.

During the off period the liposomal amikacin formulation is not administered to the patient. In some embodiments, the off period is 15 days or longer, for example, 15 to 75 days, 15 to 35 days, or 20 to 35 days. In other embodiments, the off period is 20 to 30 days, 25 to 35 days or 25 to 30 days. In other embodiments, the off period is about 25, 26, 27, 28, 29 or 30 days. In other embodiments, the off period is about 28 days, while in still other embodiments, the off period is at least 29 days.

In some embodiments, the off period is of 25 to 75 days, 35 to 75 days, or 45 to 75 days. In other embodiments, the off period is 50 to 75 days, 50 to 70 days, 50 to 65 days or 50 to 60 days. In other embodiments, the off period is about 50, 51, 52, 53, 54, 55, 56, 57, 58, 59 or 60 days, while in other embodiments, the off period is about 56 days.

In some embodiments, the administration period is about 28 days and the off period is about 28 days, while in other embodiments, the administration period is about 28 days and the off period is about 56 days.

In some embodiments, the effective dose comprises 250 to 1,500 mg of amikacin, 250 to 1000 mg of amikacin, 250 to 750 mg of amikacin, or 250 to 700 mg amikacin each day of the administration period. In other embodiments, the effective dose is about 280 to about 560 mg of amikacin. In other embodiments, the effective dose is about 230 mg to about 330 mg, or about 510 mg to about 610 mg. In other embodiments, the effective dose of amikacin is about 100, 150, 200, 250, 300, 250, 400, 450, 500, 550, 600, 650, 700 or 750 mg of amikacin daily. In other embodiments, the effective dose is about 280 or about 560 mg of amikacin.

In some embodiments, the administration period is about 28 days, and the dose is about 280 to about 560 mg of amikacin. In other embodiments, the administration period is about 28 days, the off period is about 28 days, and the dose is about 280 to about 560 mg. In other embodiments, the administration period is about 28 days, the off period is about 56 days, and the dose is about 280 o about 560 mg.

In some embodiments, the pulmonary disorder is selected from the group consisting of chronic obstructive pulmonary disease, bronchiectasis, pulmonary infection, cystic fibrosis, alpha-l-antitrypsin enzyme deficiency and a combination thereof. In some embodiments, the pulmonary condition is cystic fibrosis. In other embodiments, the pulmonary condition is a bacterial pulmonary infection, *Pseudomonas* (e.g., *P. aeruginosa, P. paucimobilis, P. putida, P. fluorescens*, and *P. acidovorans*), staphylococcal, Methicillin-resistant *Staphylococcus aureus* (MRSA), streptococcal (including by *Streptococcus pneumoniae*), *Escherichia coli, Klebsiella, Enterobacter, Serratia, Haemophilus, Yersinia pesos, Burkholderia pseudomallei, B. cepacia, B. gladioli, B. multivorans, B. vietnamiensis, Mycobacterium tuberculosis, M. avium* complex (MAC) (*M. avium* and *M. intracellulare*), *M kansasii, M. xenopi, M marinum, M. ulcerans,* or *M. fortuitum* complex (*M. fortuitum* and *M. chelonei*) infections. In some embodiments, the infection is a *P. aeruginosa* infection, while in other embodiments, the infection is a non-tuberculous mycobacterial infection. The pulmonary infection may or may not be associated with cystic fibrosis. Thus, in some embodiments, the pulmonary condition is both cystic fibrosis and a pulmonary infections such as *P. aeruginosa*. In other embodiments, the pulmonary conditions is bronchiectasis. The bronchiectasis may or may not be associated with cystic fibrosis.

The present method provides advantageous levels of amikacin at the site of the pulmonary disorder, while limiting systemic exposure to the drug, and also provides a sustained benefit to the subject for surprisingly extended periods of time. While not being bound by any particular theory, it is believed that administration of liposomal amikacin in accordance the with methods described herein results a "depot" effect in the lungs of the subject. Specifically, it is believed that the liposome particles are small enough and contain an appropriate lipid formulation to penetrate and diffuse through CF sputum and into the bacterial biofilm. The liposomes shield the entrapped cationic amikacin in neutral liposomes to minimize electrostatic interaction with the negatively charged sputum/biofilm, which would otherwise reduce its bioavailability. In addition, there are *P. aeruginosa* derived virulence factors (rhamnolipids) (Davey et al. 2003), which release amikacin the liposomes. Therefore, it is hypothesized that relatively high concentrations of drug can be delivered locally to the bacterial macro-colony environment.

Additionally, it is believed that inhalation of liposomal amikacin leads to a dose dependent recruitment of macrophages as an adaptive response to inhalation of drug/lipid formulation. The presence of alveolar macrophages (which have been shown to be functionally normal in liposomal amikacin treated rats) may be particularly beneficial in CF patients. CF patients are known to have reduced number of macrophages in their lungs and possibly with poor functionality, which may contribute to the chronicity of *P. aeruginosa* lung infection, and to the higher prevalence of non-tuberculous mycobacterial infection in this population. The dose dependent recruitment of macrophages may also contribute to the sustained effects observed using the methods of the present invention. Specifically, the macrophages in the lung may take up liposomal amikacin, and then remain in the lung for a period of time, followed by release of the liposomal amikacin by the macrophages. A clinical study (described in the exemplification below) of liposomal amikacin in CF patients chronically infected with *P. aeruginosa* has demonstrated safety, tolerability and dose dependent improvement in lung function and respiratory symptoms; and reduction of sputum bacterial density at the end of 28 days of treatment. This improvement in lung function was sustained for at least 28 days after completion of treatment (Day 56) with a 560 mg dose of liposomal amikacin, indicating a sustained treatment effect.

The present method thus provides, in some embodiments, advantageous levels of amikacin in the blood and in the sputum. For example, the methods provides relatively low systemic exposure to amikacin, while providing high, sustained levels of amikacin at the site of the pulmonary condition. For example, in some embodiments, the patient has a serum $C_{max}$ of amikacin of less than about 25 mcg/mL during the administration period. In other embodiments, the serum $C_{max}$ is less than 20, 15, 10, 5 or 2 mcg/mL during the administration period.

In some embodiments, the patient has a sputum $C_{max}$ of amikacin of at least about 500 mcg per gram of sputum either during the administration, or for a sustained period of time, such as at least 15 days, after the administration. In other embodiments, the sputum $C_{max}$ of amikacin is at least 750, 1000, 1500, 2000, 2500, 3000 or 3500 mcg per gram of sputum.

When the pulmonary disorder includes a pulmonary infection, the present invention also provides a reduction in the colony forming units of the bacteria in the lung for a sustained period of time. For example, the CFU's are reduced compared to a baseline value. In some embodiments, the patient has a reduction in $\log_{10}$ CFU of the bacterial infection in the lungs of at least about 0.5 for at least 15 days after the administration period ends. In other embodiments, the reduction in the $\log_{10}$ CFU is at least by 1.0, 1.5, 2.0 or 2.5. *Pseudomonas* infections, in particular, can form large colonies, known as "mucoid" *Pseudomonas*, particularly in patients with cystic fibrosis. In some embodiments, the CFU's are reduced as described above in a mucoid strain of a *Pseudomonas* infection.

In some embodiments, the patient experiences an improvement in lung function for at least 15 days after the administration period ends. For example, the patient may experience an increase in the forced expiratory volume in one second ($FEV_1$), an increase in blood oxygen saturation, or both. In some embodiments, the patient has an $FEV_1$ that is increased by at least 5% or at least 10% over the $FEV_1$ prior to the treatment cycle. In other embodiments, $FEV_1$ is increased by 5 to 50%, 5 to 25%, or 5 to 20%. In other embodiments, $FEV_1$ is increased by 5 to 15% or 5 to 10%. In other embodiments, $FEV_1$ is increased by 10 to 50%, 10 to 40%, 10 to 30% or 10 20%. $FEV_1$ is frequently measured in mL. Accordingly, in some embodiments, $FEV_1$ is increased by at least 25 mL when compared to $FEV_1$ prior to the treatment. In some embodiments, $FEV_1$ is increased by 25 to 500 mL, 25 to 400, 25 to 300 or 25 to mL. In other embodiments, $FEV_1$ is increased by 50 to 500 mL, 50 to 400 mL, 50 to 300 mL, 50 to 200 mL or 50 to 100 mL.

In some embodiments, blood oxygen saturation is increased in the subject compared to the blood oxygen saturation levels prior to the administration. In some embodiments, blood oxygen saturation is increased by at least 1% or by at least 2% for at least 15 days after the administration period. In other embodiments, the blood oxygen saturation levels are increased by about 1 to 50%, 1 to 25%, 1 to 20%, 1 to 15%, 1 to 10% or 1 to 5%. In other embodiments, the blood oxygen saturation levels are increased by about 2 to 10% or 2 to 5%.

The aforementioned sustained periods of time may be at least 20, 25, 30, 35, 40, 45, 50, 55, 60, 65, 70 or 75 days after the administration period. In other embodiments, the sustained period of time is at least 28, 35, 42, 48 or 56 days after the administration period. In other embodiments, sustained period of 15 to 75 days, 15 to 35 days, or 20 to 35 days. In other embodiments, the sustained period of time is 20 to 30 days, 25 to 35 days or 25 to 30 days. In other embodiments, the sustained period of time is about 25, about 26, about 27, about 28, about 29 or about 30 days, or about 28 days, or at least 29 days. In other embodiments, the sustained period of time during is 25 to 75 days, 35 to 75 days, or 45 to 75 days. In other embodiments, the sustained period is 50 to 75 days, 50 to 70 days, 50 to 65 days or 50 to 60 days. In other embodiments, the sustain period is about 50, about 51, about 52, about 53, about 54, about 55, about 56, about 57, about 58, about 59 or about 60 days, while in other embodiments, the sustained period is about 56 days.

In some embodiments, the aforementioned methods advantageously provide a reduced incidence of pulmonary exacerbations in the patient. The method also advantageously increases the length of time to pulmonary exacerbation. For example, in some embodiments, the length of time to pulmonary exacerbation is at least about 20 days. In other embodiments, the length of time is 20 to 100 days. In other embodiments, the length of time is 25 to 100 days, 30 to 100 days, 35 to 100 days or 40 to 100 days. In other embodiments, the length of time is 25 to 75 days, 30 to 75 days, 35 to 75 days or 40 to 75 days. In other embodiments, the length of time is 30 to 60 days.

In some embodiments, the incidence of rescue treatment is reduced. In other embodiments, the length of time to rescue treatment is reduced, for example when the patient has a pulmonary infection, the time to anti-infective rescue treatment is reduced. In some embodiments, the length of time is 20 to 100 days. In other embodiments, the length of time is 25 to 100 days, 30 to 100 days, 35 to 100 days or 40 to 100 days. In other embodiments, the length of time is 25 to 75 days, 30 to 75 days, 35 to 75 days or 40 to 75 days. In other embodiments, the length of time is 30 to 60 days.

In some embodiments, the liposomal amikacin formulation used in the aforementioned methods comprises amikacin and any of the lipids described above. In some embodiments, the liposomal amikacin formulation comprises a phospholipid and a sterol, such as DPPC and cholesterol. In other embodiments, the liposomal amikacin formulation comprises DPPC and cholesterol in about a 2 to 1 ratio by weight. In some embodiments, the liposomal amikacin formulation has a lipid to drug ratio of about 0.5 to about 1.0, about 0.5 to 0.7, or about 0.6 by weight. In other embodiments, the liposomal amikacin formulation has a lipid to drug ratio of about 0.3 to about 1.0 by weight, while in other embodiments, the lipid to drug ratio is about 0.5 to 0.7 by weight, or about 0.65 by weight. The liposomes in the formulation may have a amend diameter of 100 to 1000 nm, 100 to 500 nm, 200 to 500 nm, or about 300 nm. In some embodiments, the total concentration of amikacin in the liposomal amikacin formulation is about 20 to 100 mg/mL, 20 to 90 mg, mL, 30 to 90 mg/mL, 30 to 80 mg/mL, or 40 to 80 mg/mL. In other embodiments, the concentration is about 30, 40, 50, 60, 70, 80 or 90 mg/mL.

In some embodiments, aforementioned method comprises:
  administering to the patient an effective dose of a nebulized liposomal amikacin formulation for at least one treatment cycle, wherein:
    the treatment cycle comprises an administration period of about 28 days, followed by an off period of about 28 days;
    the effective dose comprises about 280 to about 560 mg of amikacin daily during the administration period; and
    the liposomal amikacin formulation comprises DPPC and cholesterol in about a 2:1 ratio, and a lipid to amikacin ratio of about 0.5 to about 0.7.

In other embodiments, the method comprises:
  administering to the patient an effective dose of a nebulized liposomal amikacin formulation for at least one treatment cycle, wherein:
    the treatment cycle comprises an administration period of about 28 days, followed by an off period of about 56 days;
    the effective dose comprises about 280 to about 560 mg of amikacin daily during the administration period; and
    the liposomal amikacin formulation comprises DPPC and cholesterol in about a 2:1 ratio, and a lipid to amikacin ratio of about 0.5 to about 0.7.

In other embodiments, the present invention relates to a method of providing a sustained treatment effect in a subject comprising: administering to the patient an effective dose of a nebulized liposomal amikacin formulation for at least one treatment cycle, wherein: the treatment cycle comprises an administration period of 15 to 75 days, followed by an off period of 15 to 75 days; and the effective dose comprises 100 to 2500 mg of amikacin daily during the administration period.

In another embodiment, the present invention relates to a method of improving oxygen saturation levels in a patient with a pulmonary condition comprising: administering to the patient an effective dose of a nebulized liposomal amikacin formulation for at least one treatment cycle, wherein: the treatment cycle comprises an administration period of 15 to 75 days, followed by an off period of 15 to 75 days; and the effective dose comprises 100 to 2500 mg of amikacin daily during the administration period.

In another embodiment, the present invention relates to a method of improving $FEV_1$ in a patient with a pulmonary condition comprising: administering to the patient an effective dose of a nebulized liposomal amikacin formulation for at least one treatment cycle, wherein: the treatment cycle comprises an administration period of 15 to 75 days, followed by an off period of 15 to 75 days; and the effective dose comprises 100 to 2500 mg of amikacin daily during the administration period.

In another embodiment, the present invention relates to a method of reducing bacterial density in the lung or sputum of a patient with a bacterial pulmonary infection comprising: administering to the patient an effective dose of a nebulized liposomal amikacin formulation for at least one treatment cycle, wherein: the treatment cycle comprises an administration period of 15 to 75 days, followed by an off period of 15 to 75 days; and the effective dose comprises 100 to 2500 mg of amikacin daily during the administration period, and wherein the bacterial density remains reduced for at least 15 days after the last day of the administration.

EXAMPLES

Introduction to Materials and Methods

Lipid based or liposomal aminoglycoside, such as amikacin, formulations for inhalation are sustained-release formulations of aminoglycosides encapsulated inside nanoscale liposomal carriers designed for administration via inhalation. Sustained-release targeting of high concentrations of amikacin in the lungs and biofilm penetration properties of these formulations have several advantages over inhalation of the "free" antibiotic, e.g., inhaled tobramycin. Amikacin can be encapsulated in liposomes composed of dipalmitoylphosphatidylcholine (DPPC) and cholesterol, at a targeted lipid-to-drug ratio of about 0.6-0.7:1 (w/w). An example of a ~70 mg/mL liposomal amikacin formulation useful in the aforementioned methods is presented below:

| Component | Concentration |
| --- | --- |
| Amikacin[1] | ~70 mg/mL |
| Dipalmitoylphosphatidylcholine (DPPC) | ~30 mg/mL |
| Cholesterol | ~15 mg/mL |
| 1.5% NaCl | QS |

[1]Added to the formulation as Amikacin sulfate, USP.

These formulations can be prepared according to the methods described in U.S. Publication No. 20060073198 or 20080089927, both of which are hereby incorporated by reference.

These formulations have several advantages in treating pulmonary conditions, for example, CF subjects with chronic infection caused by *P. aeruginosa*, including:
1. The ability to attain a prolonged antibiotic effect of amikacin in the lung by achieving high concentrations and a prolonged half life due to sustained release.

2. The ability to target and increase the effective concentration of amikacin in the lung with low systemic levels of the aminoglycoside.
3. The potential to better target bacteria growing in a biofilm as a result of unique properties of lipid based or liposomal aminoglycosides.
4. Additional release of the drug at the site of infection in the lungs of CF patients, due to targeted action of secreted phospholipase C and rhamnolipids from bacteria and/or phospholipase A2 or defensins from activated polymorphonuclear leukocytes.
5. Amikacin is a semisynthetic aminoglycoside with a unique resistance to aminoglycoside inactivating enzymes. Consequently, some *P. aeruginosa* strains which are resistant to tobramycin will likely remain susceptible to amikacin.
6. Amikacin has less binding affinity than other aminoglycosides for megalin, the transporter responsible for renal cortical aminoglycoside accumulation, and thus inherently has a lower potential for nephrotoxicity.
7. The increase in both the half life, and the area under the concentration curve (AUC) of lipid based or liposomal amikacin, along with biofilm penetration should allow for less frequent administration, enhanced bactericidal activity and reduced potential for selection of resistant organisms.

Preclinical pharmacokinetics have demonstrated that the AUC (0-48 hr) of amikacin in the lungs of rats that received a 60 mg/kg dose aerosol of Liposomal Amikacin was five-fold higher than the AUC of tobramycin in the lungs of rats that received an equal dose of tobramycin by inhalation. Generally, 10% of the administered antibiotic is deposited in the lungs for rats. Conversely, the AUC of drug in the kidneys of rats that received an equal dose of tobramycin was significantly higher than the kidney AUC of rats that received aerosols of Liposomal Amikacin. Additionally, data from 30-day inhalation toxicology studies in rats and dogs suggest that there will be no safety pharmacology issues with inhaled Liposomal Amikacin.

In 14 days rat model studies of *pseudomonas* infection, it was noted that 60 mg/kg of Liposomal Amikacin (75 mg/mL) administered every other day for 14 days (Q2D×7), which effectively delivered half the cumulative dose of aminoglycoside than the other groups, was as effective as 60 mg/kg of Liposomal Amikacin given once per day, and Tobramycin given twice per day daily for 14 days. With 28 day dosing in this model, there were equivalent reductions in CFUs in animals receiving Liposomal Amikacin dosed daily at ~60 mg/kg or dosed every other day at ~120 mg/kg. Liposomal Amikacin administered at 120 mg/kg once a day for 14 days was as effective as Tobramycin 60 mg/kg/day (administered twice a day) for 28 days, which suggests a higher AUC and possibly a prolonged post-antibiotic effect with Liposomal Amikacin at 120 mg/kg dosed once per day (see Example 5).

The administration of Liposomal Amikacin via inhalation in the animal model resulted in increased lung (AUC) above the MIC of the bacteria, and demonstrated sustained therapeutic effect, with a reduced frequency, and duration of dosing as compared to Tobramycin. Importantly, the preclinical data for Liposomal Amikacin appear supportive of the hypothesis that this specific formulation may be advantageous over other inhalation products that are hindered by a rapid clearance from lung tissue, necessitating frequent dosing (Geller, Pitlick et al. 2002), which poses a burden for patients and might limit patient compliance.

Additionally, clinical experience demonstrated that nebulized Liposomal Amikacin 50 mg/mL administered as 500 mg once per day for 14 days is well tolerated, and elicits a clinically relevant effect on pulmonary function and decrease in *P. aeruginosa* density in CF patients. Also, evaluation of the PK data indicates the systemic exposure to Liposomal Amikacin, even at the 500 mg dose, is very low. By either Cmax or AUC or mg of aminoglycoside which is recovered in the urine, the observed systemic exposure to amikacin, associated with Liposomal Amikacin, given by inhalation is approximately $\frac{1}{3}$ to $\frac{1}{4}$ the exposure seen with 600 mg/d of TOBI and is less than $\frac{1}{200}$ compared to normal parenteral doses of amikacin. The data further indicate high levels of amikacin are achieved in the sputum. Median AUC values for sputum were 290 and 980 fold greater than the median AUC values for serum on day 1 and day 14 respectively.

Inhaled liposomal amikacin maintains prolonged targeted lung exposures and enhance the uptake of drug to the site of infection. Using data from a human clinical Phase 1b/2a study in which CF patients who were chronically infected with *P. aeruginosa* received multiple doses of Liposomal Amikacin 50 mg/ml, the objectives of the analyses described herein were three-fold: (1) to use population pharmacokinetic (PK) modeling to characterize amikacin systemic exposure, including approximate systemic bioavailability; (2) to characterize the disposition of liposomal amikacin in sputum; and 3) to characterize the pharmacokinetic-pharmacodynamic (PK-PD) relationship between change in forced expiratory volume in one second ($FEV_1$), change in percent predicted forced expiratory volume in one second ($FEV_1\%$ predicted), forced expired flow between 25-75% of forced vital capacity ($FEF_{25-75}\%$), and forced vital capacity (FVC), in *P. aeruginosa* colony forming units (CFU) relative to baseline at Days 7 and 14, and amikacin exposure.

Preclinical Studies with Liposomal Amikacin

Several preclinical studies were conducted with the 20 and 50 mg/mL formulations. Anti-pseudomonas activity of Liposomal Amikacin in in vitro and in vivo models was demonstrated. Additionally, studies confirmed that virulence factors secreted by *Pseudomonas* facilitate the further release of amikacin from the liposomes, and characterized the deposition and sustained release of amikacin in the lungs of rats, and dogs. The safety of a 30 day administration of Liposomal Amikacin in two species was also established.

Nonclinical pharmacokinetics have demonstrated that the AUC (0-48 hr) of amikacin in the lungs of rats that received a 60 mg/kg dose of Liposomal Amikacin via nebulization, was five-fold higher than the AUC of tobramycin in the lungs of rats that received an equal dose of tobramycin by inhalation. High levels of amikacin were sustained in the lung (>250 µg/mL through 150 hr), suggesting a depot effect. In contrast, lung levels of tobramycin were undetectable within 6 hours of cessation of administration. Conversely, the AUC of drug in the kidneys of rats that received an equal dose of tobramycin was significantly higher than the AUC of rats that received aerosols of Liposomal Amikacin. There were no significant differences in the AUC of aminoglycosides in the serum and urine of the animals; serum levels were undetectable after 24 hr. This profile supports the intended sustained release and depot effect of amikacin in the lung following administration of nebulized Liposomal Amikacin, potentially representing an enhanced efficacy profile. These data for Liposomal Amikacin appear supportive of the hypothesis that this specific formulation may be advantageous over other inhalation products that are hindered by a rapid clearance from lung tissue, necessitating frequent dosing (Geller, Pitlick et al. 2002), and placing a burden on patients. Additionally, toxicokinetic data from 30-day inhalation GLP toxicology studies in rats and dogs showed that there is a 15 fold increase in lung deposition of amikacin dogs as compared to the free amikacin treated group, with comparable plasma and urine levels, indicating high lung concentrations with low systemic exposure.

The pharmacodynamic effect of Liposomal Amikacin was evaluated in vivo in a rat model of chronic pulmonary infection with *Pseudomonas* (Cash, Woods et al. 1979). In a 14 days *Pseudomonas* infection model, 60 mg/kg of Liposomal Amikacin (75 mg/mL) was administered every other day for 14 days (Q2D×7). This regimen was as effective as 60 mg/kg of Liposomal Amikacin (given once per day for 14 days), and tobramycin (given twice per day for 14 days). When dosing was extended to 28 days, there were equivalent reductions in CFUs for animals receiving Liposomal Amikacin dosed daily at ~60 mg/kg or dosed every other day at ~120 mg/kg. Also, in this experiment, Liposomal Amikacin administered at 120 mg/kg once a day for 14 days was as effective as tobramycin 60 mg/kg/day (administered twice a day) for 28 days. This indicated a higher AUC and a prolonged post-antibiotic effect with Liposomal Amikacin at 120 mg/kg dosed once per day. The preclinical pharmacodynamic data were thus consistent with a sustained antimicrobial benefit enhanced by the site-specific delivery of drug to the lungs via inhalation.

Thus, administration of Liposomal Amikacin via inhalation resulted in increased lung concentrations (AUC) several fold above the MIC of the bacteria, with the potential to provide a sustained therapeutic effect with a reduced frequency and duration of dosing, particularly as compared to Tobramycin.

Example 1

Phase 1b/2a Study

Data used for this population PK analysis were obtained from two human clinical Phase 1b/2a studies in which CF patients, chronically infected with *P. aeruginosa*, were administered a total of 500 mg of Liposomal Amikacin daily (in two 20 minute sessions with a 5 minute rest period in between) for 14 days.

Amikacin serum samples were obtained pre-dose, and 1, 2, 4, 6, 8, 12 and 24 hours post-dose on Days 1 and 14, while urine samples were collected over 6 hour intervals on Day 1 and Day 14 for a period of 24 hours. Sputum samples were also collected on Day 1 and Day 14, soon after the dose was administered, between 4 and 6 hours after dosing and prior to dose administration on the following day, as well as on Days 14, 21, and 28. Serum, sputum and urine samples were assayed for amikacin using Liquid Chromatography-Mass Spectrometry/Mass Spectrometry (LC-MS/MS).

Pulmonary function tests (PFT) were carried out during screening from Day-14 to 0) and at baseline (i.e., prior to dose administration on Day 1) and on Day 1, 7, 14, 21, 28, 35, and 42. Sputum samples for microbiology were also collected at baseline and on each of these days. Additional PFTs were carried out 1.5 hours and 3 hours post-dose on Day 1 and Day 14.

Pharmacokinetic Analysis

The data were fit by candidate PK models, using Monte Carlo Parametric Expectation Maximization (MC-PEM), as is implemented in S-ADAPT 1.53, initially fitting the plasma concentrations, then co-modeling the serum and urine data. Model discrimination was based on the fit of the data and change in objective function. The 24 hour area under the curve (AUC) at steady state for serum amikacin values were calculated using the post-hoc parameter estimates from the final population PK model. Covariate relationships between patient demographics and individual post-hoc parameters were assessed first graphically, then by means of statistical models created using SYSTAT® 11 (SYSTAT Software, Inc., Richmond, Calif.). Sputum AUC values from 0 to 24 hours on Day 1 and Day 14 were obtained using the linear trapezoidal rule.

Dependent variables for the PK-PD analysis included the change in PFT values for $FEV_1$, $FEV_1\%$ predicted, $FEF_{25-75\%}$ and FVC, on Day 7 and 14 relative to baseline (prior to dose administration on Day 1) and the change in $\log_e$ CFU on each of these days relative to baseline. Independent variables evaluated included the ratio of the average 24 hour AUC for serum and sputum to the baseline minimum inhibitory concentration (MIC), AUC:MIC ratio for *P. aeruginosa*. The average 24 hour serum and sputum AUC was computed by taking the average of the Day 1 and Day 14 AUC values.

Using a one-sample t-test, the statistical significance of mean changes from baseline for each of the above-described dependent variables was assessed. Using Spearman's rank correlation ($r_s$), the direction and strength of the relationship between each of the dependent variables and AUC:MIC ratio for serum and sputum was assessed. The direction and strength of the relationship between change in each of the PFT values from baseline and change in $\log_{10}$ CFU from baseline were also assessed.

Results

A total of 24 patients completed the two studies with 13 patients from Study 1 and 11 patients from Study 2. The median (min, max) age of all the patients was 23.7 (14, 38) years with a median (range) creatinine clearance (CrCL) at baseline of 126 (76.8, 173) mL min/1.73 m².

The most robust fit to the serum concentration data was obtained using a two-compartment model (one absorption site, the lung, and the central compartment) with zero-order drug input into the lungs, a first-order process from lungs to the central compartment and linear elimination. Allowing inter-occasional variation on apparent total clearance (CLt/F) and apparent central volume of distribution (Vc/F) between Day 1 and Day 14 improved the objective function statistically. Urine data was modeled by fitting the amounts of amikacin recovered in the collection intervals, as a function of serum concentrations and renal clearance (CLr). Table 1 is a summary of the fitted PK parameter values.

TABLE 1

Structural population pharmacokinetic model for liposomal amikacin for inhalation with inter-occasional variability - Parameter estimates and standard errors.

| Parameter | Population mean | | Inter-individual variability (% CV) | |
|---|---|---|---|---|
| | Final estimate | % SE | Final estimate | % S E |
| CLt/F Day 1 (L/hr) | 68.4 | 10.3 | 48.7 | 29.9 |
| Vc/F Day 1 (L) | 286 | 12.3 | 59.0 | 29.7 |
| ka (hr⁻¹) | 3.34 | 32.5 | 99.8 | 50.5 |
| CLr (L/hr) | 3.40 | 15.4 | 63.9 | 36.7 |
| CLt/F Day 14 (L/hr) | 45.2 | 8.01 | 37.1 | 30.7 |
| Vc/F Day 14 (L) | 250 | 8.51 | 27.0 | 30.8 |
| SDint$_{serum}$ | 0.05 | 6.02 | | |
| SDS1P$_{Urine}$ | 0.70 | 9.16 | | |
| SDint$_{Urine}$ | 0.03 | | | |

Minimum value of the objective function = −258.6

The goodness of fit for observed versus Bayesian post-hoc individual fitted serum concentration data was excellent, with an overall r2 of 0.98.

The AUC values for the serum and sputum data are shown in Tables 2 and 3, respectively. Median AUC values for sputum were 286 and 978 fold greater than the median AUC values for serum on Day 1 and Day 14, respectively. As evidenced by the higher CV % values, greater variability was evident in sputum (117% on Day 1 and 91.2% on Day 14) compared to serum AUC (51.9% on Day 1 and 42.4% on Day 14) values.

TABLE 2

Summary of serum AUC values[1] - All patients

| Study Day | N | Mean | SD | Min | Median | Max |
|---|---|---|---|---|---|---|
| Day 1 | 24 | 8.27 | 4.29 | 3.67 | 6.88 | 20.1 |
| Day 14 | 24 | 12.0 | 5.08 | 5.65 | 10.8 | 30.1 |

[1]AUC values in mcg/mL · hr

TABLE 3

Summary of sputum AUC values[1] - All patients

| Study Day | N | Mean | SD | Min | Median | Max |
|---|---|---|---|---|---|---|
| Day 1 | 20 | 3830 | 4500 | 78.70 | 1970 | 17200 |
| Day 14 | 19 | 12500 | 11400 | 1740 | 10578 | 50000 |

[1]AUC values are in mcg/mL · hr

Serum ($r^2=0.98$) and urine ($r^2=0.38$) concentrations were well and modestly fit by model, respectively. On Day 7, 14 and 21, the observed change for $FEF_{25-75\%}$ was 0.49 (p<0.001), 0.42 (p=0.02) and 0.34 L/sec (p=0.04), respectively. On Day 7 and 14, the observed change for $FEV_1$ was 0.24 (p=0.002) and 0.13 L (p=0.10), respectively, and was 7.49 (p<0.001) and 4.38 L/sec (p=0.03) for $FEV_1\%$ predicted. Significant relationships (p≤0.05) between $\log_{10}$ CFU and serum AUC:MIC ratio, and between changes in $\log_{10}$ CFU and $FEV_1$, $FEV_1\%$ predicted and FVC were identified.

Baseline and Day 14 PFT data were available for all 24 patients and for PFTs carried out on Day 7 and 21, such data were available for 23 patients. Microbiology data were available for all 24 patients. Since MIC values collected prior to dosing on Day 1 for Study 2 were not reported, the screening MIC values as well as CFU counts were used as baseline values.

Using a one-sample t-test, the statistical significance of mean changes from baseline for each of the above-described dependent variables was assessed. Using Spearman's rank correlation ($r_s$), the direction and strength of the relationship between each of the dependent variables and AUC:MIC ratio for serum and sputum was assessed.

Mean changes in PFT values on Day 7 relative to baseline were statistically significant for all PFT endpoints. Mean changes in $FEV_1\%$ predicted and $FEF_{25-75\%}$ on Day 14 relative to baseline were also statistically significant (p=0.029 and p=0.016, respectively). By Day 21, mean change in $FEF_{25-75\%}$ relative to baseline was the single PFT that remained statistically significant (p=0.036). Regardless of the study day considered, mean change in $\log_{10}$ CFU from baseline was not statistically significant.

As shown in Table 4, correlations between change in PFT values from baseline and either sputum or serum AUC:MIC ratio were not statistically significant, regardless of whether changes on Day 7 or 14 were evaluated. As shown in Table 5, the correlation between change in $\log_{10}$ CFU from baseline and serum AUC:MIC ratio was statistically significant for both Day 7 or 14. Increasing serum AUC:MIC ratios were associated with larger decreases in $\log_{10}$ CFU on Day 7 ($r_s=-0.46$, p=0.048) and 14 ($r_s=-0.45$, p=0.048) relative to baseline.

Correlations between change in both PFT value and $\log_{10}$ CFU on Day 7 and 14 relative to baseline were statistically significant for $FEV_1$, $FEV_1\%$ predicted, and FVC (p<0.05).

TABLE 4

Relationship between change in pulmonary function test values from baseline and AUC:MIC ratio for serum and sputum - All patients

| Study Day AUC:MIC | Spearman's rank correlation | Change in PFT values from baseline | | | |
|---|---|---|---|---|---|
| | | $FEV_1$ | $FEV_1\%$ predicted | $FEF_{25-75\%}$ | FVC |
| Day 7 serum | $r_s^2$ | 0.072 | 0.0066 | <0.0001 | 0.021 |
| | p value | 0.21 | 0.71 | 0.97 | 0.51 |
| Day 14 serum | $r_s^2$ | 0.046 | 0.0073 | 0.00018 | 0.0012 |
| | p value | 0.31 | 0.69 | 0.95 | 0.87 |
| Day 7 sputum | $r_s^2$ | 0.033 | 0.040 | 0.0085 | 0.19 |
| | p value | 0.46 | 0.41 | 0.71 | 0.06 |
| Day 14 sputum | $r_s^2$ | 0.025 | 0.052 | 0.0053 | 0.06 |
| | p value | 0.51 | 0.35 | 0.77 | 0.31 |

TABLE 5

Relationship between change in $\log_{10}$ CFU and AUC:MIC ratio for serum and sputum - All patients

| Study Day AUC:MIC | Spearman's rank correlation | $\log_{10}$ CFU |
|---|---|---|
| Day 7 serum | $r_s^2$ | 0.021 |
| | p value | 0.048 |
| Day 14 serum | $r_s^2$ | 0.20 |
| | p value | 0.048 |
| Day 7 sputum | $r_s^2$ | 0.017 |
| | p value | 0.64 |
| Day 14 sputum | $r_s^2$ | 0.0031 |
| | p value | 0.84 |

While mean change in $\log_{10}$ CFU of *P. aeruginosa* from baseline on both Day 7 and 14 was not statistically significant, the correlation between change in $\log_{10}$ CFU from baseline at both of these time points and serum AUC:MIC ratio was statistically significant; increases in serum AUC:MIC ratio were associated with decreases in $\log_{10}$ CFU. In contrast, this relationship did not hold with sputum AUC:MIC and confirms the large variability in sputum kinetics of Liposomal Amikacin, that is also shown with TOBI (Geller, Pitlick et al. 2002).

The significant relationships between changes in $\log_{10}$ CFU and serum AUC:MIC ratio, and between changes in PFT values and $\log_{10}$ CFU, and the lack of significant decrease in $\log_{10}$ CFU of *P. aeruginosa* during the two weeks of treatment with liposomal amikacin for inhalation suggests that higher doses may be required to be more reliably effective in a large patient population.

Summary of the Phase 1a/2b Study

Two Phase 1b/2a studies using the Liposomal Amikacin 50 mg/mL have been completed. The two studies were similar in design. A total of 24 CF patients (with $FEV_1 \geq 40\%$ of predicted) received 500 mg Liposomal Amikacin daily for 14 days. The drug was administered using a PARI LC Star nebulizer, over a period of two 20-minute inhalation sessions with a 5 minute rest period between sessions. There were 13 patients enrolled in Study 1 and 11 patients in Study 2. Patient demographics were similar, with the exception of *Pseudomonas* MICs at baseline. In Study 1, the mean MIC (μg/mL) was 8 (range 1.5-16) and in Study 2, the mean MIC was 41 μg/mL (range 8-192). The patients enrolled in Study 2 had prior experience with inhalation antibiotics, and per protocol, were permitted to resume treatment with TOBI®/Colistin after Day 28 of the study. The patients in Study 1 were naïve to inhalation antibiotics, and did not receive additional inhalation antibiotics during the follow-up period. The 500 mg dose of Liposomal Amikacin (50 mg/mL) was well tolerated, and in select patients improved pulmonary function and decreased the density of *P. aeruginosa* in sputum. The details of patient demographics for Studies 1 and 2 (combined) are shown in Table 6.

TABLE 6

Patient demographics in studies 1 and 2.

| Variable | Mean | SD | Median | Min | Max |
|---|---|---|---|---|---|
| Age | 23.7 | 6.96 | 22.5 | 14.0 | 38.0 |
| Weight (kg) | 59.1 | 13.0 | 58.6 | 43.4 | 99.6 |
| Height (cm) | 168 | 8.10 | 168 | 155 | 194 |
| IBW (kg) | 61.4 | 8.99 | 60.0 | 47.9 | 87.7 |
| CrCL (mL/min) | 125 | 20.9 | 126 | 76.8 | 173 |

All efficacy analyses in these human clinical Phase 1b/2a studies were exploratory in nature. The efficacy endpoints included:

Change from Baseline in density of *P. aeruginosa* ($log_{10}$ CFU/g) in sputum;

Change from Baseline in pulmonary function tests ($FEV_1$, $FEV_1\%$ predicted, FVC, and $FEF_{(25-75\%)}$ Changes in *P. aeruginosa* sputum density, $FEV_1$, and $FEV_1\%$ predicted at Day 14 were identified as the primary efficacy endpoints.

Quantitative culture of sputum samples and subsequent amikacin susceptibility testing of each morphologically distinct *P. aeruginosa* were performed. The MIC of amikacin for the isolates with the highest MIC cultured from each subject at screening and Day 14 was documented. The density (CFU per gram of sputum) of *P. aeruginosa* in sputum was calculated as the $log_{10}$ value for the sum of all morphotypes.

A summary of the baseline characteristics for the combined population (n=24) are shown in Table 7.

TABLE 7

Baseline measurements for patients in Studies 1 and 2.

| Variable | Mean | SD | Median | Min | Max |
|---|---|---|---|---|---|
| FEV1 (L) | 2.38 | 1.07 | 2.18 | 1.15 | 6.10 |
| Predicted FEV1 % (L/sec) | 65.5 | 18.9 | 62.5 | 40.0 | 119 |
| FEF25-75 (L/sec) | 1.71 | 1.26 | 1.49 | 0.55 | 5.50 |
| FVC (L) | 3.32 | 0.92 | 3.27 | 1.67 | 5.28 |
| Log10 CFU Count | 7.05 | 1.3 | 7.3 | 3.51 | 8.98 |
| MIC (mcg/mL) | 35 | 56 | 10 | 2 | 192 |

Study 1: In this study CF patients infected with *P. aeruginosa* isolates sensitive to amikacin (amikacin MIC<64 µg/mL), and those subjects naïve to inhaled antibiotics were enrolled. Administration of Liposomal Amikacin 500 mg once daily for 2 weeks showed a mean change in log sum of counts of *P. aeruginosa* from baseline to Day 14 of 1.09 (n=13; 95% confidence interval, 2.09 to 0.09). The reductions in counts were observed in 9 of the 13 subjects. Treatment with Liposomal Amikacin did not result in selection of resistant strains of *P. aeruginosa*. The mean *P. aeruginosa* amikacin MIC was 8.04 µg/mL at Day 0 and 30.79 µg/mL at Day 14. On Day 14, a single isolate in one subject had a non sensitive MIC (>25 µg/mL); all other Day 14 isolates were sensitive to amikacin. No human was hospitalized or received intravenous anti-*Pseudomonas* antibiotics. Additionally, there was improvement in lung function as measured by an increase in $FEV_1$ from baseline to Day 14 of +260 mL (n=13; 95% confidence interval, +30 mL to +500 mL). The corresponding change in FEV1% predicted from baseline to Day 14 was +7.32%. Increases in FEV1 were observed in 9 of the 13 subjects. Also noted were increases in $FEF_{(25-75\%)}$ (mean: 570 mL) and FVC (mean: 180 mL).

Study 2: Study 2 was conducted in a population of CF patients who were infected with *P. aeruginosa*, and were inhalation antibiotic treatment experienced. In these patients, the administration of Liposomal Amikacin 500 mg q.d. for 2 weeks did not show any significant change in *P. aeruginosa* density during the study (p-values≥0.297 for change from Day 1). The proportion of patients with mucoid *P. aeruginosa* remained constant throughout the study. No statistically significant changes in $FEV_1$, $FEV_1\%$ predicted, FVC, and $FEF_{(25-75\%)}$ were observed after administration of Liposomal Amikacin 500 mg. Nevertheless, trends suggesting improvement in $FEV_1\%$ predicted, FVC, and $FEF_{(25-75\%)}$ were observed at Day 7, Day 14 (end of treatment), and Day 15.

Integrated Efficacy Summary: Studies 1 and 2

Data from the combined population of 24 patients in studies 1 and 2 are summarized below in Tables 8, 9, 10, and 11. The microbiologic end-point of change in log CFU of *P. aeruginosa*, demonstrated a reduction in bacterial density in the combined population, but this did not achieve statistical significance. But, when data were analyzed from the inhalation antibiotic naïve patients (study 1), a statistically significant reduction in CFU was observed at end of treatment. Factors that might explain this effect are the inherent variability in sputum samples, the inter-laboratory variability in methodology, and reporting of quantitative microbiology, and the enrollment of patients with higher MICs (including resistant isolates) in study 2. All of the above are further compounded by the small sample size of each study.

Assessment of clinical benefit by measurement of pulmonary function tests showed a statistically significant improvement in lung function as measured by an increase in $FEV_1$ from baseline to Day 7 of +240 mL (n=23; p-value 0.0024). The effect at day 14 was a 126 mL increase from baseline in FEV1, which was not statistically significant. A corresponding statistically significant increase in FEV1% predicted from baseline to Day 7 was +7.49% (n=24; p-value 0.0002), and at Day 14 was +4.37% (n=24; p-value 0.0285). The improvement in lung function was also noted with the assessment of small airways as measured by $FEF_{(25-75\%)}$ at day 7, an increase in +494 mL (n=23; p-value 0.001), and at Day 14, +423 mL (n=24; p-value 0.0162). These data support a clinically meaningful improvement in lung function in CF patients with chronic *Pseudomonas* infection who have received a 14 day course of treatment with Liposomal Amikacin.

TABLE 8

Change in FEV from baseline at various times in all patients.

| Time Point | N | Mean | CV | p-value |
|---|---|---|---|---|
| Day 7 (pre dose) | 23 | 0.24 | 1.4 | 0.0024 |
| Day 14 (pre-dose) | 24 | 0.126 | 2.86 | 0.1006 |
| Day 21 | 23 | 0.073 | 4.91 | 0.3397 |

TABLE 9

Change in % predicted FEV from baseline at various times in all patients.

| Time Point | N | Mean | CV | p-value |
|---|---|---|---|---|
| Day 7 (pre dose) | 23 | 7.491 | 1.09 | 0.0002 |
| Day 14 (pre-dose) | 24 | 4.379 | 2.10 | 0.0285 |
| Day 21 | 23 | 2.713 | 3.25 | 0.1544 |

TABLE 10

Change in $FEF_{25-75}$ from baseline at various times in all patients.

| Time Point | N | Mean | CV | p-value |
|---|---|---|---|---|
| Day 7 (pre dose) | 23 | 0.494 | 1.26 | 0.001 |
| Day 14 (pre-dose) | 24 | 0.423 | 1.89 | 0.0162 |
| Day 21 | 23 | 0.338 | 2.15 | 0.0361 |

TABLE 11

Change in CFU from baseline at various times in all patients.

| Time Point | N | Mean | CV | p-value |
|---|---|---|---|---|
| Day 7 | 19 | −0.154 | −7.37 | 0.5616 |
| Day 14 | 20 | −0.315 | −4.42 | 0.3242 |
| Day 21 | 20 | 0.24 | 5.4 | 0.4182 |

Example 2

Phase 1 Clinical Study

Two Phase 1 single dose clinical studies were completed with 20 and 50 mg/mL formulations of Liposomal Amikacin in healthy volunteers and in CF patients, respectively. Six healthy volunteers received a single dose of 120 mg of Liposomal Amikacin and tolerated it well, and exhibited prolonged retention of the radiolabeled liposomes in the lungs, with a measured half-life of 46 hours.

Liposomal Amikacin was administered to CF subjects with chronic *P. aeruginosa* infections in a human clinical Phase I study (Study 3). Single doses of 90 mg (n=6), 270 mg (n=6), or 500 mg (n=4) were administered to CF subjects to evaluate the safety, tolerability and pharmacokinetics of liposomal amikacin for inhalation. A total of 24 patient dosing sessions of a single dose administration of Liposomal Amikacin or placebo by inhalation via the Pari LC Star nebulizer were evaluated. Two serious adverse events were reported (both occurring in placebo group). Both events recovered without sequelae. A total of 41 adverse events (AEs) were experienced by 17 of the 24-patient sessions dosed (71%) during the trial. Of the AEs reported, 10 of the 16 patients (62.5%) who reported adverse events were in the active group and 7 of the 8 patients (87.5%) were in the placebo group. Headache was the most common AE reported in the active group and no patients were discontinued from the study due to AEs. Liposomal Amikacin was well tolerated and safe up to a single dose of 500 mg administered via inhalation.

Additionally, the PK data confirm minimal systemic drug levels, and high sputum levels of drug, and pharmacodynamic modeling estimates long elimination half life presumably due to slow release from liposomes.

Example 3

Phase 2 Clinical Study

Figure 4:
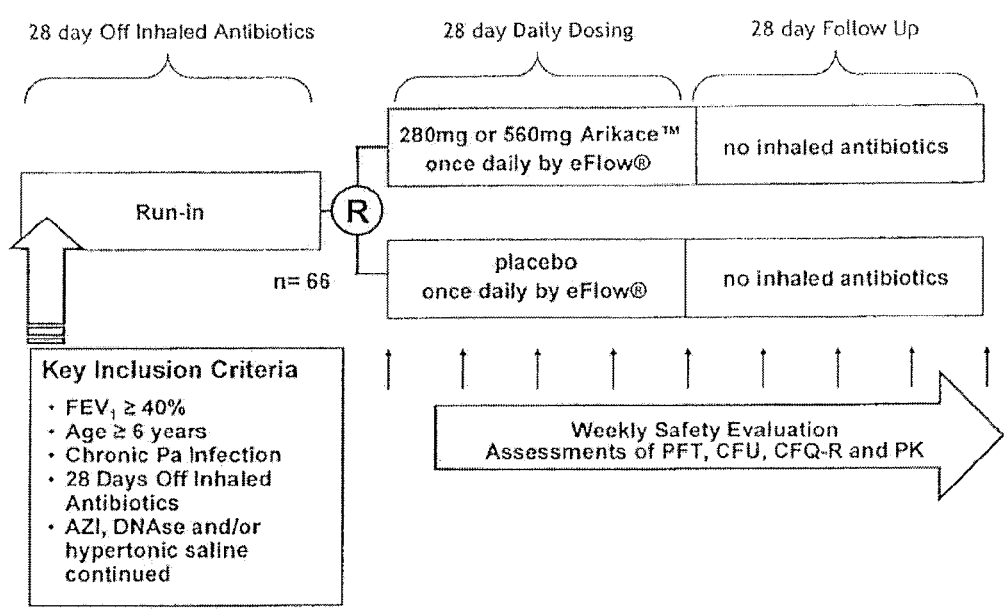
FIG. 4 depicts the study designs for Study 4, wherein patients received liposomal amikacin daily for 28 days, followed by monitoring for a 28 day period after the last day of administration.

The study design is summarized in FIG. 4. Patients included in the study were CF patients greater than or equal to six years in age with chronic *P. aeruginosa* infections. Patients were off inhaled antibiotics for 28 prior to beginning the study. Patients were stratified by baseline FEV1(% pred) and randomized 2:1 to ARIKACE® (liposomal amikacin) or placebo (1.5% NaCl). Cohort1 received 280 mg and Cohort2, 560 mg of active drug or placebo for 28 d by inhalation with PARIeFlow® nebulizer, and were followed for 28 d during which no inhaled antibiotics were administered. Safety, pharmacokinetics, Pa sputum density, Quality of Life (CFQ-R) and exacerbation rate were evaluated weekly during the study period of 56 days.

In summary, daily administration of 280 mg and 560 mg liposomal amikacin for 28 days appeared safe and well-tolerated. Administration of liposomal amikacin at 280 mg and 560 mg for 28 days results in a dose-dependent improvement in lung function, which is sustained at least for 28 days after the completion of the dosing. The patients receiving liposomal amikacin experienced fewer pulmonary exacerbations (7.14%) compared to those receiving a placebo (18.18%). Additionally, the time to exacerbation was prolonged in the amikacin groups (41 days) compared to the placebo (19 days). The groups receiving amikacin experienced no pulmonary exacerbations during the 28 day treatment period. Patients receiving liposomal amikacin demonstrated greater clinical benefit compared to the placebo group as measured by improvement in the quality of life CFQR-respiratory scale.

Figure 5:
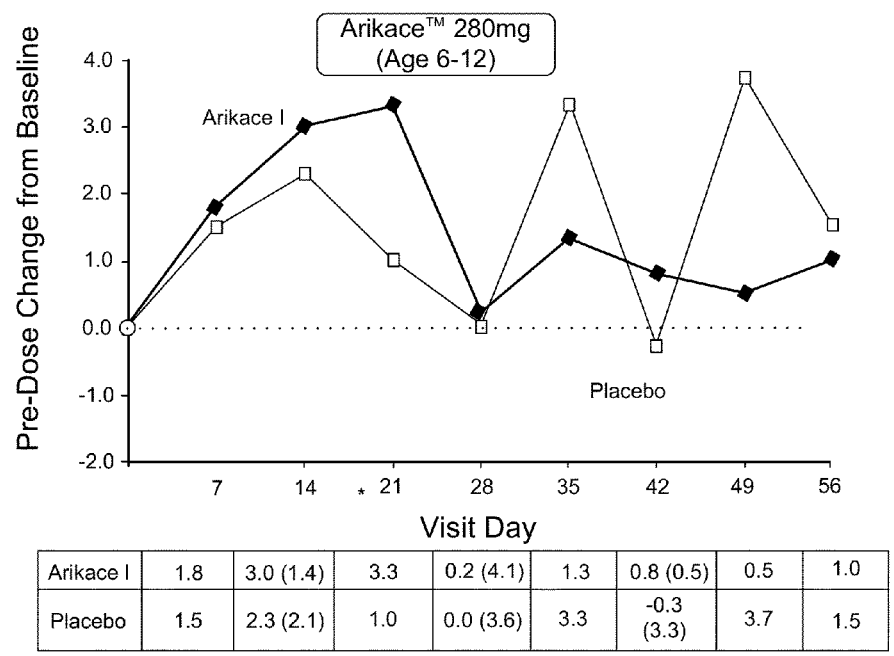
FIG. 5 depicts a graph showing the percent increase in oxygen saturation over baseline in pediatric patients receiving a 280 mg dose of amikacin compared to a placebo.
Figure 6:
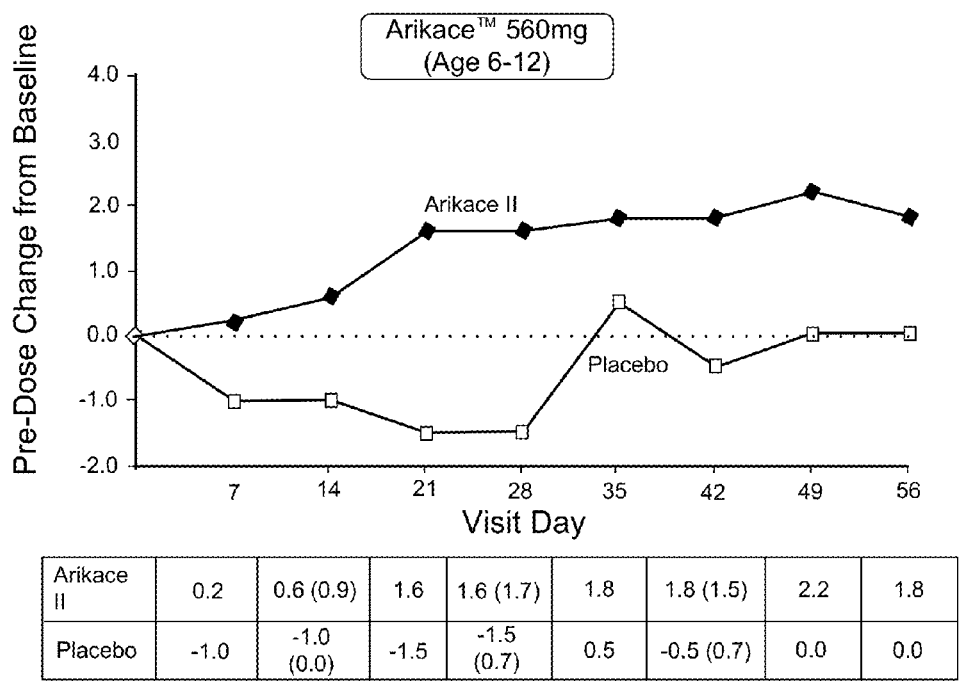
FIG. 6 depicts a graph showing the oxygen saturation in pediatric patients receiving a 560 mg dose of amikacin compared to a placebo.

FIGS. 5 and 6 depict graphs showing the change in oxygen saturation from baseline in pediatric patients (ages 6 to 12) compared to placebo. The results demonstrate an improvement in oxygen saturation beginning during the 28 day treatment period and continuing beyond the treatment period. A similar improvement in oxygen saturation was observed in patients over the age of 12 as well.

Figure 7A:
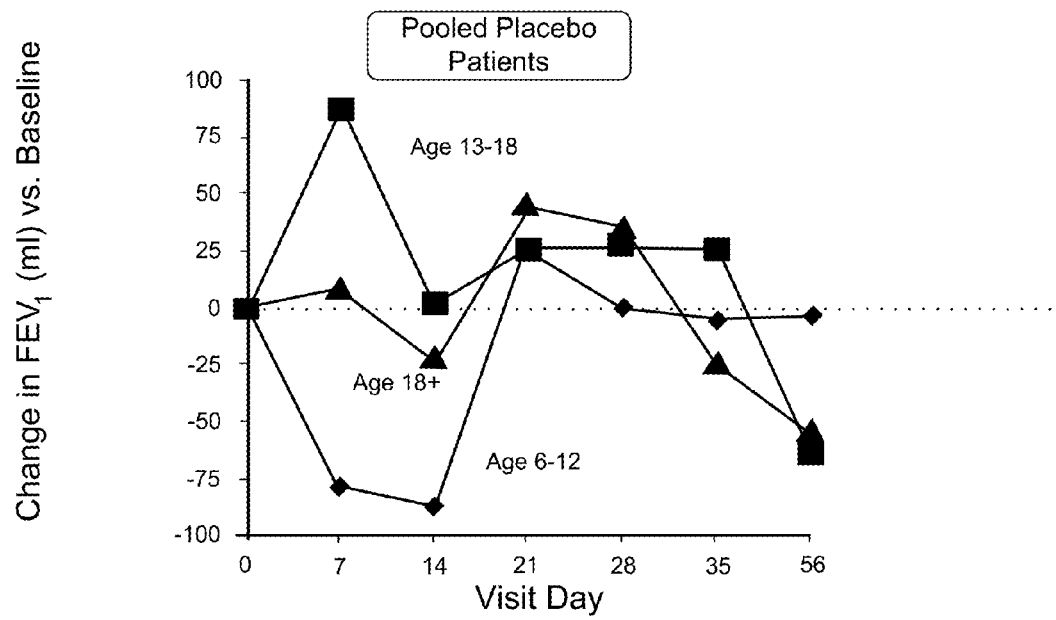
FIG. 7a depicts a graph of lung function change by age as measured by FEV1 in the placebo group. Data for placebo for both 280 and 560 mg amikacin arms of the study were pooled and divided by age. Also, data for ARIKACE® (liposomal amikacin) for 280 and 560 mg amikacin arms were pooled and divided by age.
Figure 7B:
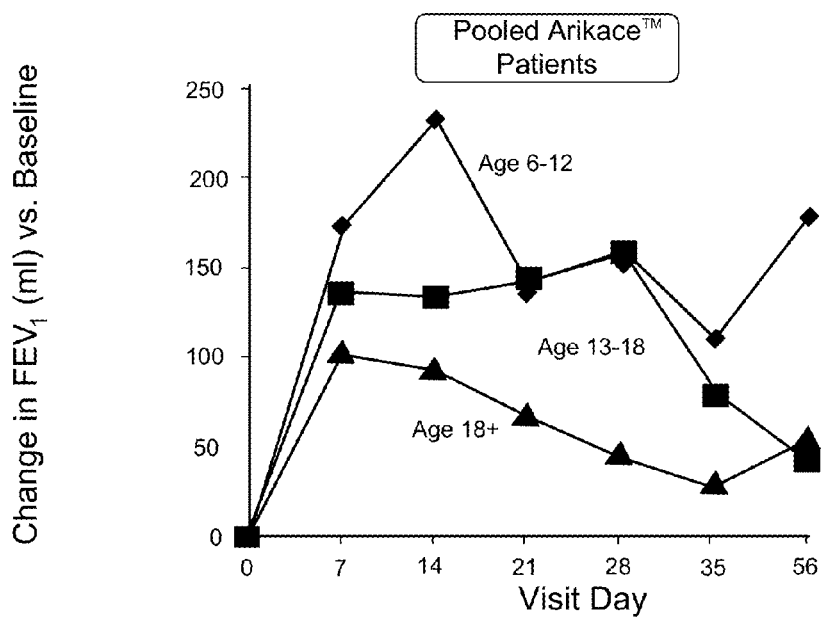
FIG. 7b depicts the lung function change by age in the patients receiving inhaled liposomal amikacin.

FIGS. 7a and 7b depict the change in lung function as measured by the forced expiratory volume ($FEV_1$) in the placebo group and the amikacin group, respectively, broken down by age groups. Patients in the placebo group show an overall decrease in $FEV_1$ by day 56, while patients receiving liposomal amikacin consistently demonstrated an increase in $FEV_1$ both during and up to 28 days after treatment. The placebo group had the following change in lung function values (measured in mL):

TABLE 12

Change in $FEV_1$ in placebo group.

| age | Day 7 | Day 14 | Day 21 | Day 28 | Day 35 | Day 56 |
|---|---|---|---|---|---|---|
| 6-12 | −79 | −88 (117) | 26 | 0 (61) | −6 | −4 |
| 13-18 | 87 | 2 (80) | 25 | 26 (149) | 25 | −65 |
| 18+ | 102 | −22 (150) | 46 | 36 (135) | −24 | −56 |

The amikacin group had the following change in lung function values (mL):

TABLE 13

Change in FEV1 in liposomal amikacin treated group.

| age | Day 7 | Day 14 | Day 21 | Day 28 | Day 35 | Day 56 |
|---|---|---|---|---|---|---|
| 6-12 | 173 | 232 (117) | 138 | 154 (165) | 110 | 178 |
| 13-18 | 136 | 133 (157) | 143 | 158 (153) | 79 | 44 |
| 18+ | 103 | 94 (107) | 68 | 46 (95) | 29 | 55 |

Figure 8:
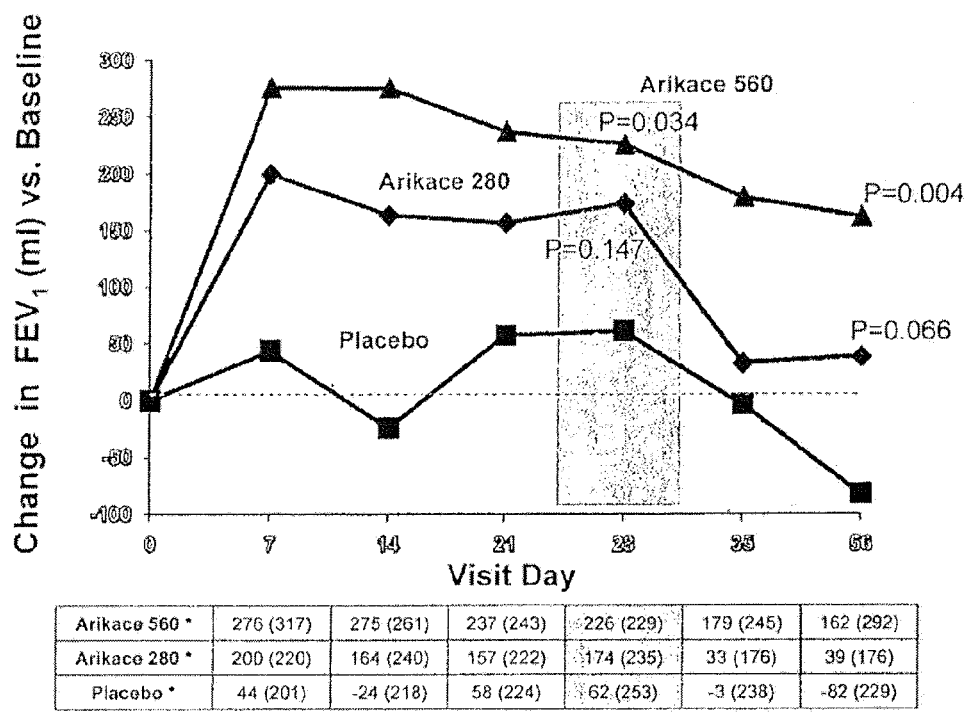
FIG. 8 depicts a graph comparing the change in FEV1 (measured in mL) in the 560 mg and 280 mg amikacin groups, and the placebo group.
Figure 9:
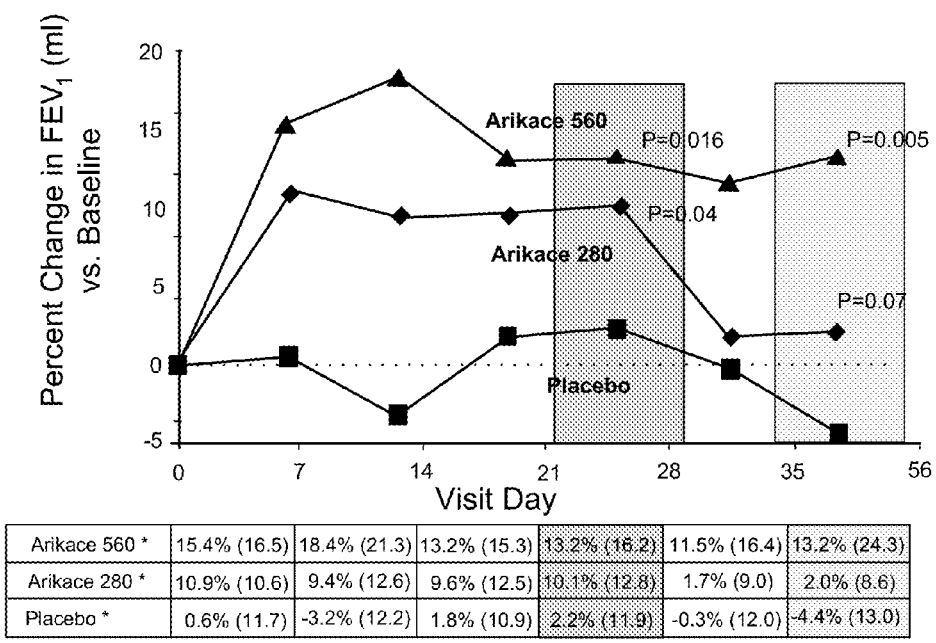
FIG. 9 depicts a graph of the change in FEV1 as a percent relative to baseline in the 560 mg amikacin, 280 mg amikacin, and placebo groups.

A comparison of the change in $FEV_1$ from baseline (measured in mL) for all patients in the 560 mg, 280 mg and placebo groups is depicted in FIG. 8. Again, the data demonstrates a sustained effect lasting as long as day 56 in patients receiving liposomal amikacin, where the effect is even more pronounced in the 560 mg group compared to the 280 mg group. FIG. 9 represents the change from baseline as a percentage. FEV1 increased significantly in the 560 mg group, with a sustained treatment effect of a 224 mL (a 17.6%) increase compared to the placebo at day 56.

Figure 10:
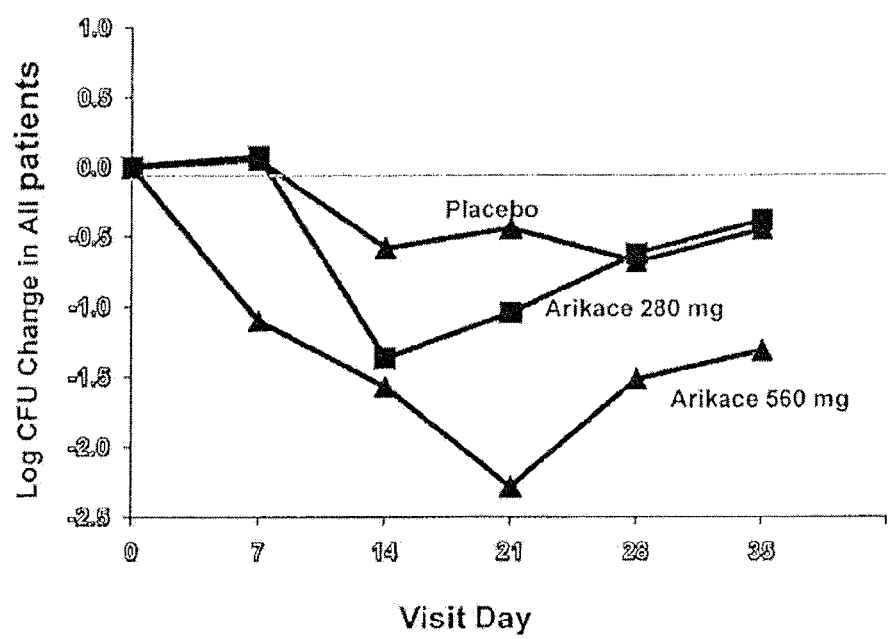
FIG. 10 depicts a graph of the Log CFU change in all patients.
Figure 11:
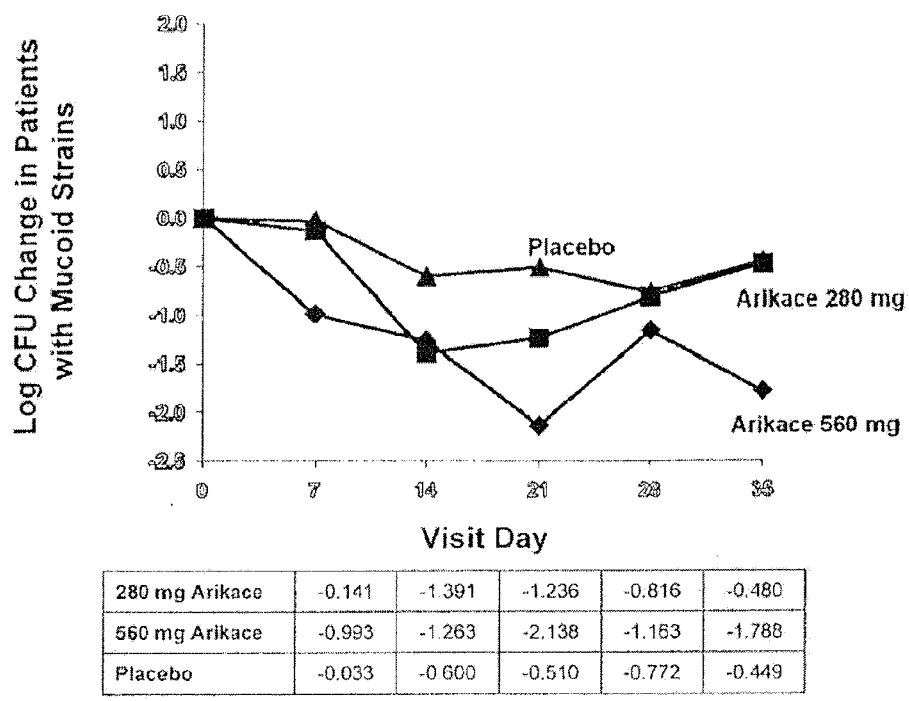
FIG. 11 depicts a graph of the Log CFU change for mucoid strains.

The data from the study also demonstrated a significant reduction in CFU's in patients receiving liposomal amikacin compared to the placebo, and this reduction was sustained at least to day 35. The reduction in CFU was more pronounced for the group receiving 560 mg of amikacin compared to the 280 mg group, as seen in FIG. 10. FIG. 11 depicts the Log CFU change for mucoid strains. These results demonstrate that *P. aeruginosa* density was reduced, as measured by log CFU, in the groups receiving liposomal amikacin, compared to placebo, and this effect was sustained at least to day 35 of the study. Patients with mucoid strains of *P. aeruginosa* also were susceptible to treatment with liposomal amikacin. A 1.2 log CFU reduction was seen in the 280 mg group, and a 2.0 log reduction in the 560 mg group. The reduction was sustained at day 35 of the 560 mg group with a 1.8 log CFU reduction, while the reduction was sustained with a log 0.4 CFU reduction in the 280 mg group.

The pharmacokinetic data revealed high levels of amikacin in the sputum of patients receiving liposomal amikacin, with the mean Cmax (CV) of 3496 (0.973) mcg/g. The mean area under the curve (AUC) value was 13,120 (1.63) mcg/g*hr for the 280 mg group, while the mean AUC was 22,445 (0.831) mcg/g*hr). The serum pharmacokinetic data, on the other hand, demonstrated low systemic exposure to amikacin, with the Cmax mean (SD) of 2.27 (1.58) mcg/mL.

Patients receiving liposomal amikacin also had a reduced frequency and time to pulmonary exacerbation. Table 14:

TABLE 14

Pulmonary Exacerbations.

|  | ARIKACE ® | Placebo |
|---|---|---|
| Patients | 3/42 (7.1%) | 3/22 (13.6%) |
| Time to exacerbation (days) | 40.6* | 19.3 |

*No exacerbation during treatment period.

As seen in Table 14, the percentage of exacerbations in patients treated with liposomal amikacin (including both the 280 mg and 560 mg groups) was lower compared to the placebo group. Moreover, the time to exacerbation was much longer in patients receiving liposomal amikacin (40.6 days) compared to 19.3 days in the placebo group.

Anti-Pseudomonal rescue treatments was also reduced in patients receiving inhaled liposomal amikacin, compared to the placebo group, as seen in Table 15.

TABLE 15

Anti-Pseudomonal rescue treatment.

|  | ARIKACE ® | Placebo |
|---|---|---|
| Patients | 4/42 (9.5%) | 3/22 (13.6%) |
| Time to exacerbation (days) | 43.0* | 21.3 |

*No rescue during treatment period.

As seen in table 15, a lower percentage of patients receiving inhaled liposomal amikacin required anti-Pseudomonal rescue treatment, compared to the placebo group.

Additionally, the time before rescue treatment was needed was reduced in the liposomal amikacin patients (43.0 days) compared to the placebo group (21.3 days).

Example 4

Nebulization of Liposomal Amikacin

The aerosol properties of Liposomal Amikacin produced from the eFlow 40 L are shown in Table 15. When compared to nebulizate generated from the LC Star, the mass median aerodynamic diameter (MMAD) values for the eFlow are ~0.5 µm larger. The actual size dependent mass distributions from both ACI (with eFlow) and NGI (with LC Star) cascade impactors for nebulized Liposomal Amikacin are shown in FIG. 1. Aerosol from the eFlow/ACI measurements was slightly narrower in size distribution than that from the LC Star/NGI. This difference is reflected in the lower mean geometric standard deviation (GSD) (1.66 versus 1.99) which is a measure of the width of the distribution around the MMAD, see values in Table 16. This narrower distribution offsets any potential effect of a larger MMAD and therefore, the amount of nebulized drug in the respirable range (<5 µm droplet size) is comparable for both eFlow and LC Star.

TABLE 16

Properties of Liposomal Amikacin Nebulized with the eFlow and LC Star Nebulizers.

|  |  | Aerosol Droplet Properties |  |  | Percent Associated Amikacin |  |
|---|---|---|---|---|---|---|
| Nebulizer | Cascade Impactor Used | MMAD (µm) | GSD (unitless) | Respirable Fraction* | Pre-Nebulization | Post-Nebulization |
| eFlow | Andersen | 3.68 ± 0.26 | 1.66 ± 0.07 | 72.9 ± 5.5 | 96.3 ± 2.1% | 66.3 ± 5.8% |
| LC Star | NGI | 3.18 ± 0.18 | 1.99 ± 0.05 | 74.5 ± 2.6 | 96.3 ± 2.1% | 62.1 ± 7.4% |

The Andersen cascade impactor was used at a flow rate of 28.3 L/min, 18° C., and 50% humidity. The NGI impactor was used at a flow rate of 15 L/min and 5° C. to achieve >60% humidity.
*Percent mass of the nominal drug dose that is less than 5 µm in diameter.

Example 5

Effect of Liposomal Amikacin on P. Aeruginosa Lung Infections in Rat

Figure 2:
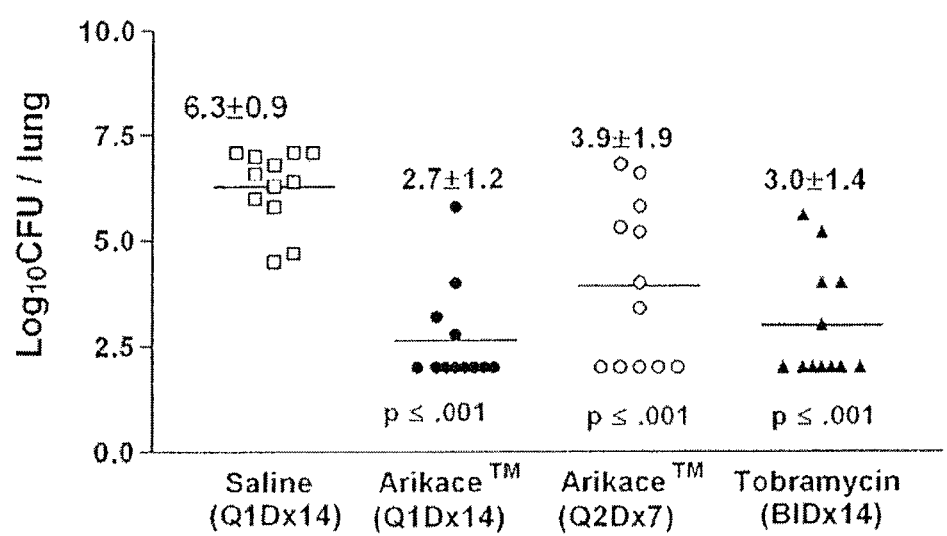
FIG. 2 depicts reduction in the $Log_{10}$ CFU/Lungs of Rats after Inhalation of Liposomal Amikacin 75 mg/mL or Tobramycin. The symbols represent the $Log_{10}$ CFU/lungs of each rat 18 days after the instillation of PA3064 in agar beads and 3 days after the last inhalation session of saline or one of the above antibiotics. The values at 2.0 $Log_{10}$ CFU represent the lower limit of detection of bacteria in the lung in the method. The bar represents the mean of each group. The means and standard deviations and two-tail t-test results were calculated using Excel software by Microsoft.

The efficacy of Liposomal Amikacin for Inhalation was studied using a model for chronic pulmonary infection (Cash, Woods et al. 1979) where P. aeruginosa, embedded in an agarose bead matrix, was instilled in the trachea of rats. This mucoid Pseudomonas animal model was developed to resemble the chronic Pseudomonas infections seen in CF patients (Cantin and Woods 1999). Rat lungs were inoculated with $10^4$ CFUs of a mucoid P. aeruginosa strain (mucoid strain 3064) originally isolated from a CF patient. Three days later, 60 mg/kg Liposomal Amikacin (75 mg/mL) was administered by inhalation once daily for 14 doses (Q1D×14) or every other day for 7 doses (Q2D×7) (6 mg/kg per dose). For comparison, tobramycin was administered by inhalation BID for 14 days (30 mg/kg per dose for a total of 60 mg/kg daily). There was a significant reduction in bacterial density in all three treatment groups as compared to the saline control (see FIG. 2). There were no significant differences in the reduction of $\log_{10}$ CFU/lung between the three treatment groups of rats. It should be noted that Liposomal Amikacin (75 mg/mL) administered every other day for 14 days (Q2D×7), which effectively delivered half the cumulative dose of aminoglycoside, was as effective as the daily dosing regimen in this model.

Figure 3:
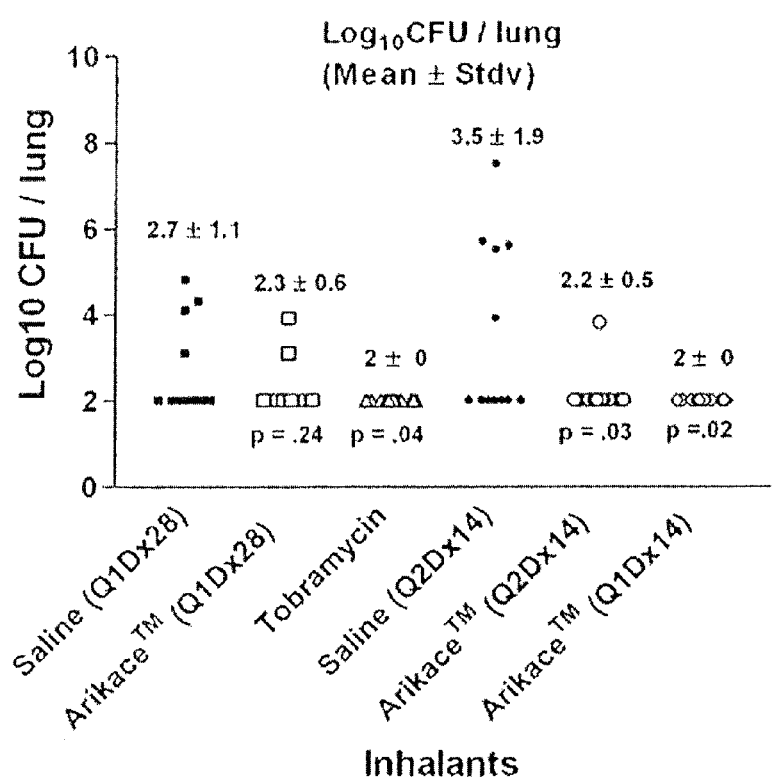
FIG. 3 depicts reduction in the $Log_{10}$ CFU/lungs of rats after Inhalation of Liposomal Amikacin and Tobramycin for 28 days. Equivalent doses of the above antibiotics were given by inhalation therapy but on different schedules. Tobramycin was given BID daily for a total of 104 min per day for 28 days. Liposomal Amikacin was given once daily for 80 min for 28 days (Q1D×28) as was saline. Liposomal Amikacin was also given once daily for 160 min every other day for 28 days (Q2D×14) or once daily for 160 min for 14 consecutive days (Q1D×14) then just observed until the rats were euthanized. The symbols represent the $Log_{10}$ CFU/lungs of each rat 35 days after the instillation of *P. aeruginosa* 3064 in agar beads. The means and standard deviations and two-tail t-test were calculated using Excel software by Microsoft).

As shown in FIG. 3, when dosing was extended in this model to 28 days, there were equivalent reductions in CFUs for animals receiving Liposomal Amikacin dosed daily at ~60 mg/kg or dosed every other day at ~120 mg/kg. Nevertheless, this was only seen as statistically significant for the latter group when compared to animals that received 1.5% saline on the same schedules (p=0.24 and 0.03, respectively). In both cases, there was a significant number of animals in the saline control groups that also experienced 2 log reductions in the CFUs. The longer duration (post 14 days) of saline inhalation treatment seemed to enhance the spontaneous ability of rats to clear their lungs of infection and presumably the agar beads which maintain the chronic infection condition. Rats that received Liposomal Amikacin ~120 mg/kg daily for 14 days, were observed for another 14 days, and then euthanized on day 35. Lungs of these animals had bacteria below the limit of detection, as was the case in the group that received tobramycin 60 mg/kg (given twice per day) daily for 28 days, and then euthanized. Data indicate that in this experiment, Liposomal Amikacin administered at 120 mg/kg once a day for 14 days was as effective as tobramycin 60 mg/kg/day (administered twice a day) for 28 days. This result suggests a higher AUC and possibly a prolonged post-antibiotic effect with Liposomal Amikacin at 120 mg/kg.

Example 6

A Multi-Cycle Study of Nebulized Liposomal Amikacin (ARIKACE®) in the Treatment of Cystic Fibrosis Patients with Chronic P. Aeruginosa Lung Infection A multi-cycle, open-label study was conducted in order to evaluate the long-term effects of multiple cycles of treatment with ARIKACE® (liposomal amikacin). The lipid component of ARIKACE® comprises the neutral lipids DPPC and cholesterol.

Figure 12:
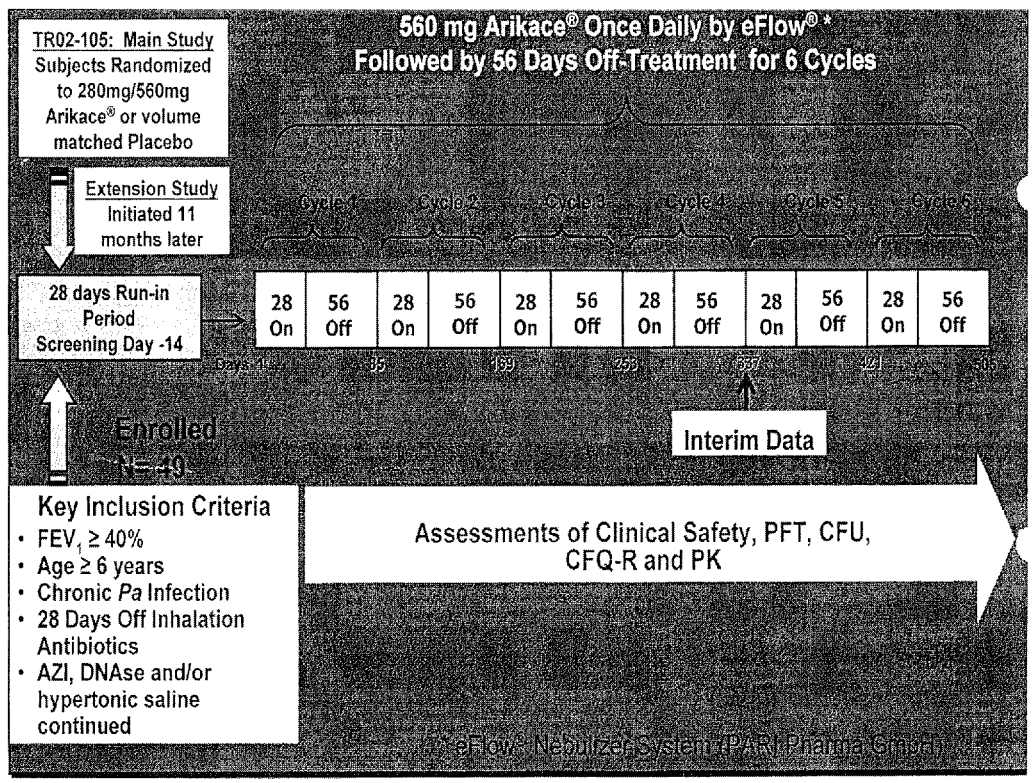
FIG. 12 depicts the study design for the multi-cycle study of nebulized liposomal amikacin, wherein patients received liposomal amikacin for 6 cycles, each consisting of 28 days of treatment with 560 mg amikacin followed by 56 days off drug.

Patients 6 years of age and above who were previously enrolled in a placebo-controlled Phase 2 study of ARIKACE® were consented to participate in this multiple cycle, 18-month study. The design of the study is shown in FIG. 12. Each cycle comprised 28 days of treatment with 560 mg of ARIKACE®, followed by 56 days off drug. ARIKACE® was administered by inhalation with PARI eFlow® nebulizer. Safety, pharmacokinetics, change in lung function, density of P. aeruginosa sputum, quality of life, and exacerbation rate were evaluated at regular intervals.

As shown in Table 17, 49 patients were enrolled in the study, and 45 patients completed six treatment cycles. Patient demographics and other baseline data are shown in Table 18. The $FEV_1$(% predicted) at baseline was 59.2%.

TABLE 17

Number of patients completing each cycle

| Number of Cycles | Number of Patients Completed Cycle (N = 49)* |
|---|---|
| Cycle 1 | 48 |
| Cycle 2 | 46 |
| Cycle 3 | 45 |
| Cycle 4 | 43 |
| Cycle 5 | 41 |
| Cycle 6 | 45 |

*Subjects enrolled in the study over 5-10 months

TABLE 18

Patient demographics and baseline data

| | | All Patients N = 49 |
|---|---|---|
| Age (yrs) | Mean (SD) | 17.4 (6.2) |
| Gender | Male | 20 (40.8%) |
| | Female | 29 (59.2%) |
| $FEV_1$ (L) | Mean (SD) | 1.871 (0.772) |
| $FEV_1$ (% Predicted) | Mean (SD) | 59.2 (19.3) |
| FVC (L) | Mean (SD) | 2.693 (1.109) |
| FEF 25-75% (L/sec) | Mean (SD) | 1.336 (0.766) |
| BMI (kg/m$^2$) | Mean (SD) | 18.425 (3.114) |

ARIKACE® administered once daily for 6 cycles was well tolerated, as adverse events were consistent with those expected in a population of CF patients. Additionally, no unexpected adverse events were observed. Overall adverse events are shown in Table 19 and Table 20 shows a listing of all adverse events by descending frequency.

TABLE 19

Overall adverse events

| | All Patients (N = 49) |
|---|---|
| Number of Adverse Events | 351 |
| Patients with Adverse Events | 48 (98.0%) |
| Number of Treatment-Related Adverse Events (Probably or Possibly Related) | 33 |
| Patients with Treatment-Related Adverse Events | 15 (30.6%) |
| Deaths | 0 (0.0%) |
| Patients with Serious Adverse Events | 15 (30.6%) |
| Patients Interrupting Study Drug Due to Adverse Events | 1 (2.0%) |

TABLE 20

Adverse events by descending frequency

| Event | All Patients (N = 49) | |
|---|---|---|
| Cystic fibrosis lung | 23 | (46.9%) |
| Cough | 14 | (28.6%) |
| Nasopharyngitis | 14 | (28.6%) |
| Haemoptysis | 11 | (22.4%) |
| Productive cough | 10 | (20.4%) |
| Rhinitis | 8 | (16.3%) |
| Dysphonia | 7 | (14.3%) |
| Influenza | 6 | (12.2%) |
| Oropharyngeal pain | 5 | (10.2%) |
| Pharyngitis | 5 | (10.2%) |
| Pyrexia | 5 | (10.2%) |
| Respiratory tract infection viral | 5 | (10.2%) |
| Abdominal pain | 4 | (8.2%) |
| Sinusitis | 4 | (8.2%) |
| Throat irritation | 4 | (8.2%) |
| Acute respiratory viral infection | 3 | (6.1%) |
| Acute Rhinitis | 3 | (6.1%) |
| Abdominal pain upper | 3 | (6.1%) |
| Blood alkaline phosphatase increased | 3 | (6.1%) |
| Headache | 3 | (6.1%) |
| Viral rhinitis | 3 | (6.1%) |

Figure 13:
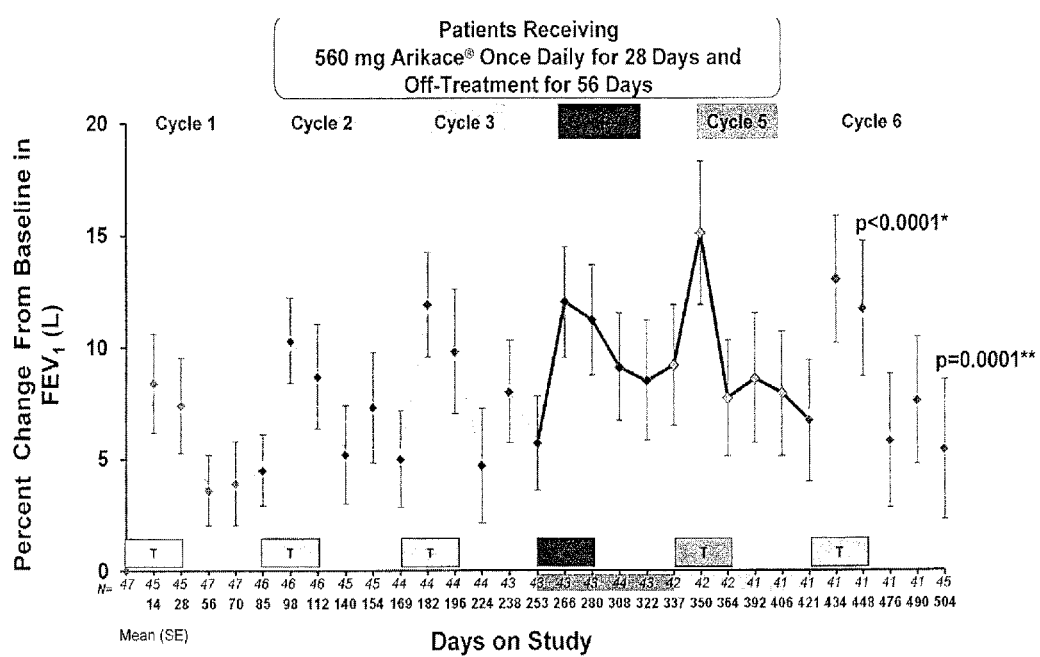
FIG. 13 depicts a graph of the change in FEV1 (measured in L) as a percent relative to baseline throughout the multi-cycle study.

The estimated relative change from baseline in $FEV_1$ to end of treatment (day 28) during cycles 1-6 was 7.9% (95% CI+4.3, +11.5%, p<0.0001). This effect was also sustained at the end of the off-treatment period (56 days) during cycles 1-6, as the estimated relative change in $FEV_1$ was 5.7% (95% CI+3.0, +8.5%, p=0.0001, FIG. 13). A statistically significant increase from baseline in $FEV_1(L)$ of 11.7% occurred by the end of the treatment portion of the $6^{th}$ cycle (p<0.0001).

Figure 14:
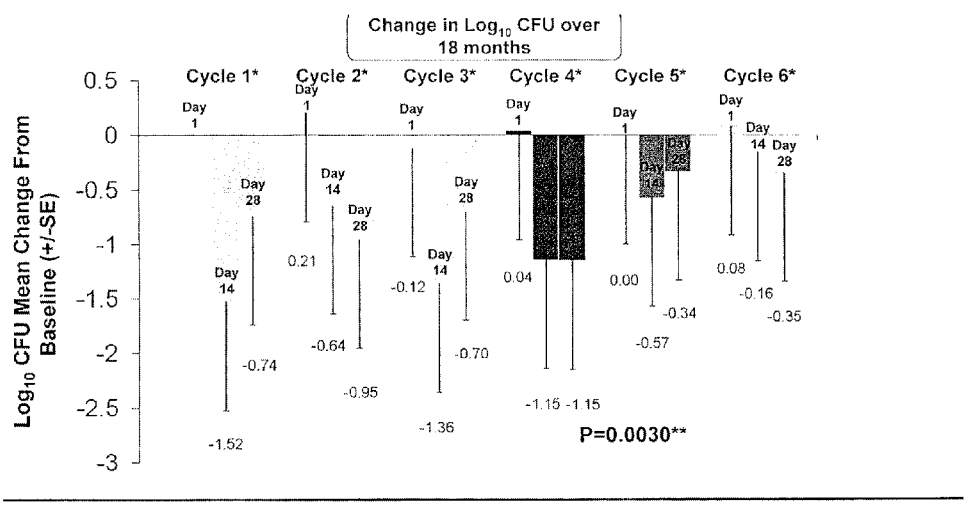
FIG. 14 depicts a graph of the change in Log CFU over the 18 months of the multi-cycle study.

Additionally, the results indicated that a significant reduction in *Pseudomonas aeruginosa* density occurred, including for mucoid strains. This effect was sustained over the treatment period of 6 cycles, with each cycle including the 56 day off period (FIG. 14). The estimated change from baseline in $log_{10}$ CFU over time was −0.58 log, (95% CI−0.21 to −0.94 log, p=0.0030).

Figure 15:
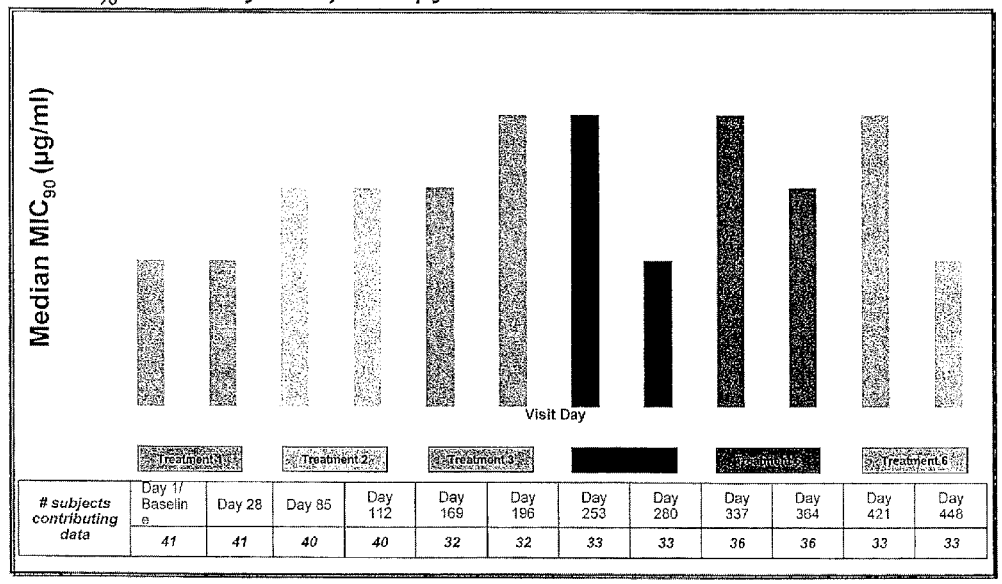
FIG. 15 depicts a graph of the median $MIC_{90}$ over six cycles of amikacin therapy.

There was also no significant shift in minimum inhibitory concentration ($MIC_{90}$) (FIG. 15).

The results of the study indicated that 560 mg ARIKACE® given once daily for 28 days followed by 56 days off drug for 6 cycles was well tolerated in cystic fibrosis patients. An increase in $FEV_1(\%)$ significantly above baseline was observed during the treatment period of each cycle, and was sustained during the 56 day off-drug period.

Example 7

Biodistribution and Clearance of Amikacin and Lipids of Liposomal Amikacin in Rat Lungs After Repeated Inhalation A study was conducted to determine the biodistribution, retention, and clearance of amikacin and liposomes in rats following multiple inhalation treatments of 90 mg/kg or 10 mg/kg liposomal amikacin (ARIKACE®). Treatment was evaluated by comparing tissue concentrations of amikacin, fluorescence of TAMRA and $DilC_{18}(5)$-DS and by microscopic evaluation of fluorescence in various sections of the lung.

CDIG female rats were randomized into three groups and received either (1) 90 mg/kg via inhalation for 27 consecutive days, (2) 10 mg/kg of liposomal amikacin via inhalation for 27 consecutive days, or (3) no treatment.

On day 28, rats in each amikacin group were administered a mixture of liposomal amikacin and fluorescently labeled liposomal amikacin (amikacin-TAMRA and $DilC_{18}(5)$-DS liposomes; 90 mg/kg) by inhalation. At 0 and 4 hours post inhalation and at 1, 3, 7, 14, 21, and 28 days post inhalation, lungs, sera, and urine were collected from 3 rats per group. The concentration of amikacin in tissues was determined by immunopolarization assays. Fluorescence was measured by spectraphotometry. TAMRA and $DilC_{18}(5)$-DS fluorescence was assessed in sera, urine, and lungs.

Lungs were separated into 3 individual right lobes and into 3 segments of each left lobe. The right caudal lobes of the lungs were frozen and later cut into thin sections (7 μm) for microscopic analysis. At each time point, unfixed tissue sections were examined for the deposition of fluorescently labeled amikacin-TAMRA and $DilC_{18}(5)$-DS liposomes using a fluorescence microscope. Images of tissues were photographed and examined for differences in fluorescence intensity.

Exposure of healthy adult rats to 28 daily multiple doses of liposomal amikacin via inhalation resulted in the uniform deposition of amikacin and liposomes throughout the lung in both 90 mg/kg and 10 mg/kg groups. The amount of amikacin deposited per gram of lung tissue was dose dependent. For each dose, the amount of amikacin deposited per gram of lung tissue was the same regardless of which lung lobe was evaluated or what section of a lobe was assayed. Amikacin was cleared from the lung uniformly. Liposomes labeled with $DilC_{18}(5)$-DS were cleared more slowly from the lungs than amikacin, resulting in the lack of measurable levels of $DilC_{18}(5)$-DS in the serum or urine. Sequenced microscopic evaluations of lung tissues dosed with dual fluorescently labeled ARIKACE® revealed that the lipid $DilC_{18}(5)$-DS within the liposomes was primarily sequestered in the macrophages within the alveolar spaces and parenchyma during the entire observation period. Amikacin-TAMRA presented as both diffused and macrophage associated fluorescence during the entire observation period.

The results of the study indicated that exposure to multiple doses of aerosolized liposomal amikacin, regardless of the dose, resulted in a uniform deposition of amikacin and liposomes throughout the entire lung followed by uniform clearance of amikacin from the lung of normal rats.

REFERENCES

1. Cash, H. A., D. E. Woods, et al. (1979). "A rat model of chronic respiratory infection with *Pseudomonas aeruginosa*." *Am Rev Respir Dis* 119(3): 453-9.
2. Challoner, P. B., M. G. Flora, et al. (2001). *Gamma Scintigraphy Lung Deposition Comparison of TOBI in the PARI LC PLUS Nebulizer and the Aerodose Inhaler*. American Thoracic Society 97th International Conference, San Francisco, Calif., Aerogen, Inc.
3. Chmiel, J. F. and P. B. Davis (2003). "State of the art: why do the lungs of patients with cystic fibrosis become infected and why can't they clear the infection?" Respir Res 4: 8.
4. Cow, G. D. (2007a). Exploratory 28 Day Inhalation Toxicity Study of SLIT™ Amikacin in Rats, Charles River Laboratories: 259.
5. Cow, G. D. and A. Morgan (2007c). 30 Day Inhalation Toxicity Study of SLIT™ Amikacin in Rats with a 30 day Recovery Period, Charles River Laboratories: 870.
6. Cow, G. D. and A. Morgan (2007d). 30 Day Inhalation Toxicity Study of SLIT™ Amikacin in Dogs with a 30 Day Recovery Period, Charles River Laboratories: 777.

7. Doring, G., S. P. Conway, et al. (2000). "Antibiotic therapy against *Pseudomonas aeruginosa* in cystic fibrosis: a European consensus." *Eur Respir J* 16(4): 749-67.
8. Geller, D. E., W. H. Pitlick, et al. (2002). "Pharmacokinetics and bioavailability of aerosolized tobramycin in cystic fibrosis." *Chest* 122(1): 219-26.
9. Gibson, R. L., J. L. Burns, et al. (2003). "Pathophysiology and management of pulmonary infections in cystic fibrosis." *Am J Respir Crit Care Med* 168(8): 918-51.
10. Gibson, R. L., J. Emerson, et al. (2003). "Significant microbiological effect of inhaled tobramycin in young children with cystic fibrosis." *Am J Respir Crit Care Med* 167(6): 841-9.
11. Gilbert, B. E., C. Knight, et al. (1997). "Tolerance of volunteers to cyclosporine A-dilauroylphosphatidylcholine liposome aerosol." *Am J Respir Crit Care Med* 156(6): 1789-93.
12. Goss, C. H. and M. Rosenfeld (2004). "Update on cystic fibrosis epidemiology." *Curr Opin Pulm Med* 10(6): 510-4.
13. Gunther, A., C. Ruppert, et al. (2001). "Surfactant alteration and replacement in acute respiratory distress syndrome." *Respir Res* 2(6): 353-64.
14. Hug, M. (2007a). Characterization of the PARI eFlow® (40 L to 50 L) and Liposomal Amikacin™ (48 to 79 mg/ml$^{(1)}$) PARI GmbH, Aerosol Research Institute: 10.
15. Hug, M. (2007b). Aerosol Characterization of the PARI eFlow® 40 L an Transave Liposomal Amikacin™ for Inhalation (70 mg/ml$^{(1)}$), PARI GmbH, Aerosol Research Institute: 12.
16. Hung, O. R., S. C. Whynot, et al. (1995). "Pharmacokinetics of inhaled liposome-encapsulated fentanyl." *Anesthesiology* 83(2): 277-84.
17. Landyshev Iu, S., A. A. Grigorenko, et al. (2002). "[Clinico-experimental aspects of liposomal therapy of bronchial asthma patients with hydrocortisone therapy]." *Ter Arkh* 74(8): 45-8.
18. Lass, J. S., A. Sant, et al. (2006). "New advances in aerosolised drug delivery: vibrating membrane nebuliser technology." *Expert Opin Drug Deliv* 3(5): 693-702.
19. Li, Z. (2007). Droplet Size of Liposomal Amikacin™: Comparison of Nebulizate for the eflow Electronic Nebulizer and the PARI LC STAR Jet Nebulizer. Monmouth Junction, Transave Inc.: 20.
20. Martini, W. Z., D. L. Chinkes, et al. (1999). "Lung surfactant kinetics in conscious pigs." *Am J Physiol* 277(1 Pt 1): E187-95.
21. Myers, M. A., D. A. Thomas, et al. (1993). "Pulmonary effects of chronic exposure to liposome aerosols in mice." *Exp Lung Res* 19(1): 1-19.
22. Niven, R. W., T. M. Carvajal, et al. (1992). "Nebulization of liposomes. III. The effects of operating conditions and local environment." *Pharm Res* 9(4): 515-20.
23. Niven, R. W. and H. Schreier (1990). "Nebulization of liposomes. I. Effects of lipid composition." *Pharm Res* 7(11): 1127-33.
24. Niven, R. W., M. Speer, et al. (1991). "Nebulization of liposomes. II. The effects of size and modeling of solute release profiles." *Pharm Res* 8(2): 217-21.
25. Ramsey, B. W., M. S. Pepe, et al. (1999). "Intermittent administration of inhaled tobramycin in patients with cystic fibrosis. Cystic Fibrosis Inhaled Tobramycin Study Group." *N Engl J Med* 340(1): 23-30.
26. Skubitz, K. M. and P. M. Anderson (2000). "Inhalational interleukin-2 liposomes for pulmonary metastases: a phase I clinical trial." *Anticancer Drugs* 11(7): 555-63.
27. Taylor, K. M., G. Taylor, et al. (1989). "The influence of liposomal encapsulation on sodium cromoglycate pharmacokinetics in man." *Pharm Res* 6(7): 633-6.
28. Ten, R. M., P. M. Anderson, et al. (2002). "Interleukin-2 liposomes for primary immune deficiency using the aerosol route." *Int Immunopharmacol* 2(2-3): 333-44.
29. Thomas, D. A., M. A. Myers, et al. (1991). "Acute effects of liposome aerosol inhalation on pulmonary function in healthy human volunteers." *Chest* 99(5): 1268-70.
30. Vecellio, L. (2006). "The Mesh Nebuliser: A Recent Technical Innovation for Aerosol Delivery." *Breath* 2(3): 253-260.
31. Vidgren, M. T., J. C. Waldrep, et al. (1994). "A study of $^{99m}$technetium-labelled beclomethasone dipropionate dilauroylphosphatidylcholine liposome aerosol in normal volunteers." *Int J Pharm:* 8.
32. Wenker, A. (2006). In vitro characterization of nebulized Amikacin, Activaero GmbH: 28.
33. Wolff, R. K. and M. A. Dorato (1993). "Toxicologic testing of inhaled pharmaceutical aerosols." *Crit Rev Toxicol* 23(4): 343-69.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of treating a *Pseudomonas aeruginosa* infection in a human patient comprising administering to the patient an effective dose of a nebulized liposomal amikacin formulation for at least one treatment cycle, wherein:
    the lipid component of the liposomal amikacin formulation comprises dipalmitoylphosphatidylcholine (DPPC) and a sterol, the at least one treatment cycle comprises an administration period of 20 to 35 days, followed by an off period of 15 to 75 days;
during which an improvement in lung function is maintained for at least 15 days after the administration period ends,
    wherein the improvement in lung function comprises an increase in Forced Expiratory Volume in one second ($FEV_1$), an increase in blood oxygen saturation, or both, as compared to the human patient prior to the at least one treatment cycle or an untreated human patient suffering from a *Pseudomonas aeruginosa* infection;
    and the effective dose comprises 510 mg to 610 mg of amikacin daily during the administration period.

2. The method of claim 1, wherein the treatment cycle is followed at least twice.

3. The method of claim 1, wherein the administration period is about 28 days.

4. The method of claim 1, wherein the off period is 15 to 35 days.

5. The method of claim 1, wherein the off period is 20 to 35 days.

6. The method of claim 1, wherein the off period is about 28 days.

7. The method of claim 1, wherein the off period is of 25 to 75 days.

8. The method of claim 1, wherein the off period is 35 to 75 days.

9. The method of claim 1, wherein the off period is 45 to 75 days.

10. The method of claim 1, wherein the off period is about 56 days.

11. The method of claim 1, wherein the administration period is about 28 days and the off period is about 28 days.

12. The method of claim 1, wherein the administration period is about 28 days and the off period is about 56 days.

13. The method of claim 1, wherein the effective dose is about 560 mg of amikacin daily during the administration period.

14. The method of claim 1, wherein the patient has a serum $C_{max}$ of amikacin of less than about 10 mcg/mL during the administration period.

15. The method of claim 1, wherein the patient has a sputum $C_{max}$ of amikacin of at least 1000 mcg per gram of sputum.

16. The method of claim 1, wherein the sputum $C_{max}$ of amikacin is at least 1000 mcg per gram of sputum during the administration.

17. The method of claim 1, wherein the sputum $C_{max}$ of amikacin is at least 1000 mcg per gram of sputum for at least 15 days after the administration.

18. The method of claim 1, wherein the patient has a reduction in $\log_{10}$ CFU of the bacterial infection in the lungs of at least 0.5 for at least 15 days after the administration period ends.

19. The method of claim 18, wherein the reduction in the $\log_{10}$ CFU is at least 1.0.

20. The method of claim 1, wherein the patient has an $FEV_1$ that is increased by at least 5% over $FEV_1$ prior to the treatment cycle.

21. The method of claim 1, wherein $FEV_1$ is increased by about 5 to about 50%.

22. The method of claim 1, wherein $FEV_1$ is increased by about 25 to about 500 mL over $FEV_1$ prior to the treatment cycle.

23. The method of claim 1, wherein blood oxygen saturation is increased by at least 1% over oxygen saturation prior to the treatment cycle.

24. The method of claim 1, wherein the time to pulmonary exacerbation in the patient is about 20 days or longer.

25. The method of claim 1, wherein the time to rescue treatment is about 20 days or longer.

26. The method of claim 1, wherein the lipid component to amikacin ratio is about 0.3 to about 1.0 by weight.

27. The method of claim 26, wherein the lipid component to amikacin ratio is about 0.5 to about 0.7.

28. The method of claim 26, wherein the lipid component to amikacin ration is about 0.6 by weight.

29. The method of claim 1, wherein the lipid component of the liposomal amikacin formulation comprises DPPC and cholesterol in about a 2 to 1 ratio by weight.

30. The method of claim 29, wherein the liposomal amikacin formulation has a lipid component to amikacin ratio of about 0.3 to about 1.0 by weight.

31. The method of claim 30, wherein the lipid component to amikacin ratio is about 0.5 to about 0.7 by weight.

32. The method of claim 30, wherein the lipid component to amikacin ratio is about 0.6 by weight.

33. The method of claim 1, wherein the human patient is a cystic fibrosis patient.

34. The method of claim 1, wherein the sterol is cholesterol.

35. The method of claim 34, wherein the liposomal amikacin formulation has a lipid to amikacin ratio of about 0.3 to about 1.0 by weight.

* * * * *